/ United States Patent /

(12) United States Patent
Phan et al.

(10) Patent No.: US 11,015,205 B2
(45) Date of Patent: May 25, 2021

(54) OLIGOMERIC VACCINES FROM PLANTS BY S-TAG-S-PROTEIN FUSIONS

(71) Applicant: Leibniz-Institut für Pflanzengenetik und Kulturpflanzenforschung (IPK), Seeland OT Gatersleben (DE)

(72) Inventors: Hoang Phan, Gatersleben (DE); Udo Conrad, Hausneindorf (DE); Thuong Thi Ho, Hanoi (VN)

(73) Assignee: Leibniz-Institut für Pflanzengenetik und Kulturpflanzenforschung (IPK), Seeland OT Gatersleben (DE)

( * ) Notice: Subject to any disclaimer, the term of this patent is extended or adjusted under 35 U.S.C. 154(b) by 60 days.

(21) Appl. No.: 16/472,802

(22) PCT Filed: Dec. 21, 2017

(86) PCT No.: PCT/EP2017/084136
§ 371 (c)(1),
(2) Date: Jun. 21, 2019

(87) PCT Pub. No.: WO2018/115305
PCT Pub. Date: Jun. 28, 2018

(65) Prior Publication Data
US 2020/0181633 A1    Jun. 11, 2020

(30) Foreign Application Priority Data
Dec. 22, 2016   (EP) .................... 16206231

(51) Int. Cl.
| | |
|---|---|
| *A61K 39/00* | (2006.01) |
| *A61K 48/00* | (2006.01) |
| *A61K 38/00* | (2006.01) |
| *C12N 9/22* | (2006.01) |
| *A61K 31/7088* | (2006.01) |
| *C12N 15/82* | (2006.01) |
| *A61K 39/12* | (2006.01) |
| *C07K 14/005* | (2006.01) |

(52) U.S. Cl.
CPC .......... *C12N 15/8258* (2013.01); *A61K 39/12* (2013.01); *C07K 14/005* (2013.01); *C07K 2319/30* (2013.01); *C07K 2319/40* (2013.01); *C12N 2760/16122* (2013.01); *C12N 2760/16134* (2013.01)

(58) Field of Classification Search
CPC .............. A61K 2300/00; A61K 38/177; A61K 38/1774; A61P 43/00; A61P 31/00
See application file for complete search history.

(56) References Cited

PUBLICATIONS

Jacquet et al., "Hydrophobin Fusion of an Influenza Virus Hemagglutinin Allows High Transient Expression in Nicotiana benthamiana, Easy Purification and Immune Response with Neutralizing activity", PLoS ONE, 9(12), 2014: pdf pp. 1-23.*
Raines et al., "The S• Tag Fusion System for Protein Purification", Methods in Enzymology, Academic Press, US, vol. 326, 2000:362-376.*
Jacquet et al., "Hydrophobin Fusion of an Influenza Virus Hemagglutinin Allows High Transient Expression in Nicotiana benthamiana, Easy Purification and Immune Response with" PLoS ONE, 2014, 9(12):1-23.*
PCT/EP2017/084136, dated Mar. 5, 2018, International Search Report and Written Opinion.
Jacquet et al., Hydrophobin fusion of an influenza virus hemagglutinin allows high transient expression in Nicotiana benthamiana, easy purification and immune response with neutralizing activity. PLoS One. Dec. 26, 2014;9(12):e115944. doi: 10.1371/journal.pone. 0115944. eCollection 2014.
McCormick et al. S-Tag: A multipurpose fusion peptide for recombinant proteins. Sep. 1, 1999. Retrieved from http://wolfson.buji. ac.il/expression/local/stag_multipurpose.pdf on Feb. 22, 2017.
Phan et al., ELPylated haemagglutinins produced in tobacco plants induce potentially neutralizing antibodies against H5N1 viruses in mice. Plant Biotechnol J. Jun. 2013;11(5):582-93. doi: 10.1111/pbi. 12049. Epub Feb. 11, 2013.
Raines et al., The S.Tag fusion system for protein purification. Methods Enzymol. 2000;326:362-76.
Rybicki, Plant-based vaccines against viruses. Virol J. Dec. 3, 2014;11:205. doi: 10.1186/s12985-014-0205-0.

* cited by examiner

*Primary Examiner* — Barry A Chestnut
(74) *Attorney, Agent, or Firm* — Heslin Rothenberg Farley & Mesiti P.C.

(57) ABSTRACT

The present invention relates to a method for production of an oligomeric protein in eukaryotic cells by co-expression of two fusion proteins in eukaryotic cells comprising a protein-S-Tag fusion protein, wherein the protein is an antigen or an antibody, and a S-protein-tail piece (tp) fusion protein. Furthermore the present invention relates to an oligomeric protein comprising at least a protein-S-Tag fusion protein and a S-protein-tail piece (tp) fusion protein, wherein the protein of the protein-S-Tag fusion protein is an antigen or an antibody, and the use in vaccines.

22 Claims, 9 Drawing Sheets
Specification includes a Sequence Listing.

SEQUENCE LISTING

<160> NUMBER OF SEQ ID NOS: 37

<210> SEQ ID NO 1
<211> LENGTH: 506
<212> TYPE: PRT
<213> ORGANISM: Avian influenza virus

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Pro Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

```
Lys Ala Ile Asp Gly Val Thr Asn Lys Val Asn Ser Ile Ile Asp Lys
        370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
                435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Lys Leu Lys Arg
                485                 490                 495

Glu Glu Ile Ser Gly Val Lys Leu Glu Gly
                500                 505

<210> SEQ ID NO 2
<211> LENGTH: 15
<212> TYPE: PRT
<213> ORGANISM: Homo sapiens

<400> SEQUENCE: 2

Lys Glu Ser Arg Ala Lys Lys Phe Gln Arg Gln His Met Asp Ser
1               5                   10                  15

<210> SEQ ID NO 3
<211> LENGTH: 15
<212> TYPE: PRT
<213> ORGANISM: Bos taurus

<400> SEQUENCE: 3

Lys Glu Thr Ala Ala Ala Lys Phe Glu Arg Gln His Met Asp Ser
1               5                   10                  15

<210> SEQ ID NO 4
<211> LENGTH: 15
<212> TYPE: PRT
<213> ORGANISM: Ovis aries

<400> SEQUENCE: 4

Lys Glu Ser Ala Ala Lys Phe Glu Arg Gln His Met Asp Ser
1               5                   10                  15

<210> SEQ ID NO 5
<211> LENGTH: 15
<212> TYPE: PRT
<213> ORGANISM: Capra hircus

<400> SEQUENCE: 5

Lys Glu Ser Ala Ala Ala Lys Phe Glu Arg Gln His Met Asp Ser
1               5                   10                  15

<210> SEQ ID NO 6
<211> LENGTH: 15
<212> TYPE: PRT
<213> ORGANISM: Sus scrofa

<400> SEQUENCE: 6
```

```
Lys Glu Ser Pro Ala Lys Lys Phe Gln Arg Gln His Met Asp Pro
1               5                   10                  15
```

<210> SEQ ID NO 7
<211> LENGTH: 15
<212> TYPE: PRT
<213> ORGANISM: Equus caballus

<400> SEQUENCE: 7

```
Lys Glu Ser Pro Ala Met Lys Phe Glu Arg Gln His Met Asp Ser
1               5                   10                  15
```

<210> SEQ ID NO 8
<211> LENGTH: 15
<212> TYPE: PRT
<213> ORGANISM: Capreolus capreolus

<400> SEQUENCE: 8

```
Lys Glu Ser Ala Ala Ala Lys Phe Glu Arg Gln His Met Asp Pro
1               5                   10                  15
```

<210> SEQ ID NO 9
<211> LENGTH: 113
<212> TYPE: PRT
<213> ORGANISM: Homo sapiens

<400> SEQUENCE: 9

```
Asp Ser Ser Pro Ser Ser Ser Thr Tyr Cys Asn Gln Met Met Arg
1               5                   10                  15

Arg Arg Asn Met Thr Gln Gly Arg Cys Lys Pro Val Asn Thr Phe Val
                20                  25                  30

His Glu Pro Leu Val Asp Val Gln Asn Val Cys Phe Gln Glu Lys Val
            35                  40                  45

Thr Cys Lys Asn Gly Gln Gly Asn Cys Tyr Lys Ser Asn Ser Ser Met
        50                  55                  60

His Ile Thr Asp Cys Arg Leu Thr Asn Gly Ser Arg Tyr Pro Asn Cys
65                  70                  75                  80

Ala Tyr Arg Thr Ser Pro Lys Glu Arg His Ile Ile Val Ala Cys Glu
                85                  90                  95

Gly Ser Pro Tyr Val Pro Val His Phe Asp Ala Ser Val Glu Asp Ser
            100                 105                 110

Thr
```

<210> SEQ ID NO 10
<211> LENGTH: 109
<212> TYPE: PRT
<213> ORGANISM: Bos taurus

<400> SEQUENCE: 10

```
Ser Thr Ser Ala Ala Ser Ser Asn Tyr Cys Asn Gln Met Met Lys
1               5                   10                  15

Ser Arg Asn Leu Thr Lys Asp Arg Cys Lys Pro Val Asn Thr Phe Val
                20                  25                  30

His Glu Ser Leu Ala Asp Val Gln Ala Val Cys Ser Gln Lys Asn Val
            35                  40                  45

Ala Cys Lys Asn Gly Gln Thr Asn Cys Tyr Gln Ser Tyr Ser Thr Met
        50                  55                  60

Ser Ile Thr Asp Cys Arg Glu Thr Gly Ser Ser Lys Tyr Pro Asn Cys
65                  70                  75                  80
```

```
Ala Tyr Lys Thr Thr Gln Ala Asn Lys His Ile Ile Val Ala Cys Glu
            85                  90                  95

Gly Asn Pro Tyr Val Pro Val His Phe Asp Ala Ser Val
            100                 105

<210> SEQ ID NO 11
<211> LENGTH: 109
<212> TYPE: PRT
<213> ORGANISM: Ovis aries

<400> SEQUENCE: 11

Ser Thr Ser Ser Ala Ser Ser Asn Tyr Cys Asn Gln Met Met Lys
1               5                   10                  15

Ser Arg Asn Leu Thr Gln Asp Arg Cys Lys Pro Val Asn Thr Phe Val
            20                  25                  30

His Glu Ser Leu Ala Asp Val Gln Ala Val Cys Ser Gln Lys Asn Val
            35                  40                  45

Ala Cys Lys Asn Gly Gln Thr Asn Cys Tyr Gln Ser Tyr Ser Thr Met
        50                  55                  60

Ser Ile Thr Asp Cys Arg Glu Thr Gly Ser Ser Lys Tyr Pro Asn Cys
65                  70                  75                  80

Ala Tyr Lys Thr Thr Gln Ala Glu Lys His Ile Ile Val Ala Cys Glu
            85                  90                  95

Gly Asn Pro Tyr Val Pro Val His Phe Asp Ala Ser Val
            100                 105

<210> SEQ ID NO 12
<211> LENGTH: 109
<212> TYPE: PRT
<213> ORGANISM: Capra hircus

<400> SEQUENCE: 12

Ser Thr Ser Ser Ala Ser Ser Asn Tyr Cys Asn Gln Met Met Lys
1               5                   10                  15

Ser Arg Asn Leu Thr Gln Asp Arg Cys Lys Pro Val Asn Thr Phe Val
            20                  25                  30

His Glu Ser Leu Ala Asp Val Gln Ala Val Cys Ser Gln Lys Asn Val
            35                  40                  45

Ala Cys Lys Asn Gly Gln Thr Asn Cys Tyr Gln Ser Tyr Ser Thr Met
        50                  55                  60

Ser Ile Thr Asp Cys Arg Glu Thr Gly Ser Ser Lys Tyr Pro Asn Cys
65                  70                  75                  80

Ala Tyr Lys Thr Thr Gln Ala Glu Lys His Ile Ile Val Ala Cys Glu
            85                  90                  95

Gly Asn Pro Tyr Val Pro Val His Phe Asp Ala Ser Val
            100                 105

<210> SEQ ID NO 13
<211> LENGTH: 109
<212> TYPE: PRT
<213> ORGANISM: Sus scrofa

<400> SEQUENCE: 13

Asp Ser Ser Ser Ser Asn Ser Ser Asn Tyr Cys Asn Leu Met Met Ser
1               5                   10                  15

Arg Arg Asn Met Thr Gln Gly Arg Cys Lys Pro Val Asn Thr Phe Val
            20                  25                  30

His Glu Ser Leu Ala Asp Val Gln Ala Val Cys Ser Gln Ile Asn Val
```

```
                35                  40                  45
Asn Cys Lys Asn Gly Gln Thr Asn Cys Tyr Gln Ser Asn Ser Thr Met
             50                  55                  60

His Ile Thr Asp Cys Arg Gln Thr Gly Ser Ser Lys Tyr Pro Asn Cys
 65                  70                  75                  80

Ala Tyr Lys Ala Ser Gln Glu Gln Lys His Ile Ile Val Ala Cys Glu
                 85                  90                  95

Gly Asn Pro Pro Val Pro Val His Phe Asp Ala Ser Val
             100                 105
```

<210> SEQ ID NO 14
<211> LENGTH: 113
<212> TYPE: PRT
<213> ORGANISM: Equus caballus

<400> SEQUENCE: 14

```
Gly Ser Thr Ser Ser Asn Pro Thr Tyr Cys Asn Gln Met Met Lys
 1               5                  10                  15

Arg Arg Asn Met Thr Gln Gly Trp Cys Lys Pro Val Asn Thr Phe Val
                 20                  25                  30

His Glu Pro Leu Ala Asp Val Gln Ala Ile Cys Leu Gln Lys Asn Ile
             35                  40                  45

Thr Cys Lys Asn Gly Gln Ser Asn Cys Tyr Gln Ser Ser Ser Met
             50                  55                  60

His Ile Thr Asp Cys Arg Leu Thr Ser Gly Ser Lys Tyr Pro Asn Cys
 65                  70                  75                  80

Ala Tyr Gln Thr Ser Gln Lys Glu Arg His Ile Ile Val Ala Cys Glu
                 85                  90                  95

Gly Asn Pro Tyr Val Pro Val His Phe Asp Ala Ser Val Glu Val Ser
             100                 105                 110

Thr
```

<210> SEQ ID NO 15
<211> LENGTH: 109
<212> TYPE: PRT
<213> ORGANISM: Capreolus capreolus

<400> SEQUENCE: 15

```
Ser Pro Ser Ser Ala Ser Ser Asn Tyr Cys Asn Gln Met Met Gln
 1               5                  10                  15

Ser Arg Asn Leu Thr Gln Asp Arg Cys Lys Pro Val Asn Thr Phe Val
                 20                  25                  30

His Glu Ser Leu Ala Asp Val Gln Ala Val Cys Phe Gln Lys Asn Val
             35                  40                  45

Ile Cys Lys Asn Gly Gln Ser Asn Cys Tyr Gln Ser Asn Ser Ala Met
             50                  55                  60

His Ile Thr Asp Cys Arg Glu Ser Gly Asn Ser Lys Tyr Pro Asn Cys
 65                  70                  75                  80

Val Tyr Lys Thr Thr Gln Ala Glu Lys His Ile Ile Val Ala Cys Glu
                 85                  90                  95

Gly Asn Pro Tyr Val Pro Val His Phe Asp Ala Ser Val
             100                 105
```

<210> SEQ ID NO 16
<211> LENGTH: 19
<212> TYPE: PRT
<213> ORGANISM: Homo sapiens -continued

<400> SEQUENCE: 16

Lys Pro Thr Leu Tyr Asn Val Ser Leu Val Met Ser Asp Thr Ala Gly
1               5                   10                  15

Thr Cys Tyr

<210> SEQ ID NO 17
<211> LENGTH: 19
<212> TYPE: PRT
<213> ORGANISM: Mus musculus

<400> SEQUENCE: 17

Lys Pro Thr Leu Tyr Asn Val Ser Leu Ile Met Ser Asp Thr Gly Gly
1               5                   10                  15

Thr Cys Tyr

<210> SEQ ID NO 18
<211> LENGTH: 19
<212> TYPE: PRT
<213> ORGANISM: Gorilla gorilla

<400> SEQUENCE: 18

Lys Pro Thr Leu Tyr Asn Val Ser Leu Val Met Ser Asp Thr Ala Gly
1               5                   10                  15

Thr Cys Tyr

<210> SEQ ID NO 19
<211> LENGTH: 19
<212> TYPE: PRT
<213> ORGANISM: Macaca mulatta

<400> SEQUENCE: 19

Lys Pro Thr Leu Tyr Asn Val Ser Leu Val Met Ser Asp Thr Ala Gly
1               5                   10                  15

Thr Cys Tyr

<210> SEQ ID NO 20
<211> LENGTH: 19
<212> TYPE: PRT
<213> ORGANISM: Canis familiaris

<400> SEQUENCE: 20

Lys Pro Thr Leu Tyr Asn Val Ser Leu Val Leu Ser Asp Thr Ala Gly
1               5                   10                  15

Glx Cys Tyr

<210> SEQ ID NO 21
<211> LENGTH: 19
<212> TYPE: PRT
<213> ORGANISM: Ailuropoda melanoleuca

<400> SEQUENCE: 21

Lys Pro Thr Leu Tyr Asn Val Ser Leu Val Leu Ser Asp Thr Ala Ser
1               5                   10                  15

Thr Cys Tyr

<210> SEQ ID NO 22
<211> LENGTH: 19
<212> TYPE: PRT
<213> ORGANISM: Oryctolagus cuniculus

```
<400> SEQUENCE: 22

Lys Pro Thr Leu Tyr Asn Val Ser Leu Ile Met Ser Asp Thr Ala Ser
1               5                   10                  15

Thr Cys Tyr

<210> SEQ ID NO 23
<211> LENGTH: 170
<212> TYPE: PRT
<213> ORGANISM: Artificial Sequence
<220> FEATURE:
<223> OTHER INFORMATION: S-protein-pII fusion protein

<400> SEQUENCE: 23

Gly Ser His His His His His Gly Ser Ser Ser Asn Tyr Cys
1               5                   10                  15

Asn Gln Met Met Lys Ser Arg Asn Leu Thr Lys Asp Arg Cys Lys Pro
                20                  25                  30

Val Asn Thr Phe Val His Glu Ser Leu Ala Asp Val Gln Ala Val Cys
            35                  40                  45

Ser Gln Lys Asn Val Ala Cys Lys Asn Gly Gln Thr Asn Cys Tyr Gln
    50                  55                  60

Ser Tyr Ser Thr Met Ser Ile Thr Asp Cys Arg Glu Thr Gly Ser Ser
65                  70                  75                  80

Lys Tyr Pro Asn Cys Ala Tyr Lys Thr Thr Gln Ala Asn Lys His Ile
                85                  90                  95

Ile Val Ala Cys Glu Gly Asn Pro Tyr Val Pro Val His Phe Asp Ala
            100                 105                 110

Ser Val Gly Pro Lys Arg Met Lys Gln Ile Glu Asp Lys Ile Glu Glu
        115                 120                 125

Ile Leu Ser Lys Ile Tyr His Ile Glu Asn Glu Ile Ala Arg Ile Lys
    130                 135                 140

Lys Leu Ile Gly Glu Arg Ala Ala Ala Glu Gln Lys Leu Ile Ser Glu
145                 150                 155                 160

Glu Asp Leu Asn Gly Ser Lys Asp Glu Leu
                165                 170

<210> SEQ ID NO 24
<211> LENGTH: 177
<212> TYPE: PRT
<213> ORGANISM: Artificial Sequence
<220> FEATURE:
<223> OTHER INFORMATION: S-protein-GCN4 fusion protein

<400> SEQUENCE: 24

Ser His His His His His Gly Ser Ser Ser Asn Tyr Cys Asn
1               5                   10                  15

Gln Met Met Lys Ser Arg Asn Leu Thr Lys Asp Arg Cys Lys Pro Val
                20                  25                  30

Asn Thr Phe Val His Glu Ser Leu Ala Asp Val Gln Ala Val Cys Ser
            35                  40                  45

Gln Lys Asn Val Ala Cys Lys Asn Gly Gln Thr Asn Cys Tyr Gln Ser
    50                  55                  60

Tyr Ser Thr Met Ser Ile Thr Asp Cys Arg Glu Thr Gly Ser Ser Lys
65                  70                  75                  80

Tyr Pro Asn Cys Ala Tyr Lys Thr Thr Gln Ala Asn Lys His Ile Ile
                85                  90                  95

Val Ala Cys Glu Gly Asn Pro Tyr Val Pro Val His Phe Asp Ala Ser
```

```
                    100                 105                 110
Val Ala Ser Gly Gly Ser Gly Gly Gly Ser Gly Gly Gly Ser Arg
            115                 120                 125

Met Lys Gln Leu Glu Asp Lys Val Glu Glu Leu Leu Ser Lys Asn Tyr
        130                 135                 140

His Leu Glu Asn Glu Val Ala Arg Leu Lys Lys Leu Val Ala Ala Ala
145                 150                 155                 160

Glu Gln Lys Leu Ile Ser Glu Glu Asp Leu Asn Gly Ser Lys Asp Glu
                165                 170                 175

Leu

<210> SEQ ID NO 25
<211> LENGTH: 147
<212> TYPE: PRT
<213> ORGANISM: Artificial Sequence
<220> FEATURE:
<223> OTHER INFORMATION: S-protein-tail piece fusion protein

<400> SEQUENCE: 25

Gly Ser Ser Ser Ser Asn Tyr Cys Asn Gln Met Met Lys Ser Arg Asn
1               5                   10                  15

Leu Thr Lys Asp Arg Cys Lys Pro Val Asn Thr Phe Val His Glu Ser
            20                  25                  30

Leu Ala Asp Val Gln Ala Val Cys Ser Gln Lys Asn Val Ala Cys Lys
        35                  40                  45

Asn Gly Gln Thr Asn Cys Tyr Gln Ser Tyr Ser Thr Met Ser Ile Thr
    50                  55                  60

Asp Cys Arg Glu Thr Gly Ser Ser Lys Tyr Pro Asn Cys Ala Tyr Lys
65                  70                  75                  80

Thr Thr Gln Ala Asn Lys His Ile Ile Val Ala Cys Glu Gly Asn Pro
                85                  90                  95

Tyr Val Pro Val His Phe Asp Ala Ser Val Ala Ser Lys Pro Thr Leu
            100                 105                 110

Tyr Asn Val Ser Leu Ile Met Ser Asp Thr Gly Gly Thr Cys Tyr Ala
        115                 120                 125

Ala Ala Glu Gln Lys Leu Ile Ser Glu Glu Asp Leu Asn Gly Ser Lys
    130                 135                 140

Asp Glu Leu
145

<210> SEQ ID NO 26
<211> LENGTH: 594
<212> TYPE: PRT
<213> ORGANISM: Artificial Sequence
<220> FEATURE:
<223> OTHER INFORMATION: H5-S-Tag fusion protein

<400> SEQUENCE: 26

Gly Ser Asp Gln Ile Cys Ile Gly Tyr His Ala Asn Asn Ser Thr Glu
1               5                   10                  15

Gln Val Asp Thr Ile Met Glu Lys Asn Val Thr Val Thr His Ala Gln
            20                  25                  30

Asp Ile Leu Glu Lys Thr His Asn Gly Lys Leu Cys Asp Leu Asp Gly
        35                  40                  45

Val Lys Pro Leu Ile Leu Arg Asp Cys Ser Val Ala Gly Trp Leu Leu
    50                  55                  60

Gly Asn Pro Met Cys Asp Glu Phe Ile Asn Val Pro Glu Trp Ser Tyr
```

-continued

```
            65                  70                  75                  80
Ile Val Glu Lys Ala Asn Pro Val Asn Asp Leu Cys Tyr Pro Gly Asp
                    85                  90                  95
Phe Asn Asp Tyr Glu Glu Leu Lys His Leu Leu Ser Arg Ile Asn His
                    100                 105                 110
Phe Glu Lys Ile Gln Ile Ile Pro Lys Ser Ser Trp Pro Ser His Glu
                    115                 120                 125
Ala Ser Leu Gly Val Ser Ser Ala Cys Pro Tyr Gln Gly Lys Ser Ser
                    130                 135                 140
Phe Phe Arg Asn Val Val Trp Leu Ile Lys Lys Asn Ser Thr Tyr Pro
145                 150                 155                 160
Thr Ile Lys Arg Ser Tyr Asn Asn Thr Asn Gln Glu Asp Leu Leu Val
                    165                 170                 175
Leu Trp Gly Ile His His Pro Asn Asp Ala Ala Glu Gln Thr Lys Leu
                    180                 185                 190
Tyr Gln Asn Pro Thr Thr Tyr Ile Ser Val Gly Thr Ser Thr Leu Asn
                    195                 200                 205
Gln Arg Leu Val Pro Arg Ile Ala Thr Arg Ser Lys Val Asn Gly Gln
                    210                 215                 220
Ser Gly Arg Met Glu Phe Phe Trp Thr Ile Leu Lys Pro Asn Asp Ala
225                 230                 235                 240
Ile Asn Phe Glu Ser Asn Gly Asn Phe Ile Ala Pro Glu Tyr Ala Tyr
                    245                 250                 255
Lys Ile Val Lys Lys Gly Asp Ser Thr Ile Met Lys Ser Glu Leu Glu
                    260                 265                 270
Tyr Gly Asn Cys Asn Thr Lys Cys Gln Thr Pro Met Gly Ala Ile Asn
                    275                 280                 285
Ser Ser Met Pro Phe His Asn Ile His Pro Leu Thr Ile Gly Glu Cys
                    290                 295                 300
Pro Lys Tyr Val Lys Ser Asn Arg Leu Val Leu Ala Thr Gly Leu Arg
305                 310                 315                 320
Asn Ser Pro Gln Arg Glu Arg Arg Gly Leu Phe Gly Ala Ile Ala Gly
                    325                 330                 335
Phe Ile Glu Gly Gly Trp Gln Gly Met Val Asp Gly Trp Tyr Gly Tyr
                    340                 345                 350
His His Ser Asn Glu Gln Gly Ser Gly Tyr Ala Ala Asp Lys Glu Ser
                    355                 360                 365
Thr Gln Lys Ala Ile Asp Gly Val Thr Asn Lys Val Asn Ser Ile Ile
                    370                 375                 380
Asp Lys Met Asn Thr Gln Phe Glu Ala Val Gly Arg Glu Phe Asn Asn
385                 390                 395                 400
Leu Glu Arg Arg Ile Glu Asn Leu Asn Lys Lys Met Glu Asp Gly Phe
                    405                 410                 415
Leu Asp Val Trp Thr Tyr Asn Ala Glu Leu Leu Val Leu Met Glu Asn
                    420                 425                 430
Glu Arg Thr Leu Asp Phe His Asp Ser Asn Val Lys Asn Leu Tyr Asp
                    435                 440                 445
Lys Val Arg Leu Gln Leu Arg Asp Asn Ala Lys Glu Leu Gly Asn Gly
                    450                 455                 460
Cys Phe Glu Phe Tyr His Lys Cys Asp Asn Glu Cys Met Glu Ser Val
465                 470                 475                 480
Arg Asn Gly Thr Tyr Asp Tyr Pro Gln Tyr Ser Glu Glu Ala Lys Leu
                    485                 490                 495
```

Lys Arg Glu Glu Ile Ser Gly Val Lys Leu Glu Gly Pro Lys Arg Met
                500                 505                 510

Lys Gln Ile Glu Asp Lys Ile Glu Glu Ile Leu Ser Lys Ile Tyr His
        515                 520                 525

Ile Glu Asn Glu Ile Ala Arg Ile Lys Lys Leu Ile Gly Glu Arg Gly
    530                 535                 540

Gly Gly Gly Ser Ala Ser Lys Glu Thr Ala Ala Ala Lys Phe Glu Arg
545                 550                 555                 560

Gln His Met Asp Ser Ala Ala Ala His His His His His His Leu Ala
                565                 570                 575

Ala Glu Gln Lys Leu Ile Ser Glu Glu Asp Leu Asn Gly Ser Lys Asp
        580                 585                 590

Glu Leu

<210> SEQ ID NO 27
<211> LENGTH: 33
<212> TYPE: PRT
<213> ORGANISM: Artificial Sequence
<220> FEATURE:
<223> OTHER INFORMATION: Trimerization domain

<400> SEQUENCE: 27

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 28
<211> LENGTH: 8074
<212> TYPE: DNA
<213> ORGANISM: Artificial Sequence
<220> FEATURE:
<223> OTHER INFORMATION: pCB301_H5-S-Tag

<400> SEQUENCE: 28
cgctcaccgg gctggttgcc ctcgccgctg ggctggcggc cgtctatggc cctgcaaacg      60
cgccagaaac gccgtcgaag ccgtgtgcga gacaccgcgg ccgccggcgt tgtggatacc     120
tcgcggaaaa cttggccctc actgacagat gaggggcgga cgttgacact tgaggggccg     180
actcacccgg cgcggcgttg acagatgagg ggcaggctcg atttcggccg gcgacgtgga     240
gctggccagc ctcgcaaatc ggcgaaaacg cctgattta cgcgagtttc cacagatga      300 tgtggacaag cctggggata agtgccctgc ggtattgaca cttgaggggc gcgactactg     360
acagatgagg ggcgcgatcc ttgacacttg aggggcagag tgctgacaga tgaggggcgc     420
acctattgac atttgagggg ctgtccacag gcagaaaatc cagcatttgc aagggttcc      480 gcccgttttt cggccaccgc taacctgtct tttaacctgc ttttaaacca atatttataa     540
accttgtttt taaccagggc tgcgccctgt gcgcgtgacc gcgcacgccg aagggggtg      600 cccccccttc tcgaaccctc ccggcccgct ctcgagttgg cagcatcacc cataattgtg     660
gtttcaaaat cggctccgtc gatactatgt tatacgccaa ctttgaaaac aactttgaaa     720
aagctgtttt ctggtattta aggttttaga atgcaaggaa cagtgaattg gagttcgtct     780
tgttataatt agcttcttgg ggtatcttta aatactgtag aaaagaggaa ggaaataata     840
aatggctaaa atgagaatat caccggaatt gaaaaaactg atcgaaaaat accgctgcgt     900

```
aaaagatacg gaaggaatgt ctcctgctaa ggtatataag ctggtgggag aaaatgaaaa    960
cctatattta aaaatgacgg acagccggta taaagggacc acctatgatg tggaacggga   1020
aaaggacatg atgctatggc tggaaggaaa gctgcctgtt ccaaaggtcc tgcactttga   1080
acggcatgat ggctggagca atctgctcat gagtgaggcc gatggcgtcc tttgctcgga   1140
agagtatgaa gatgaacaaa gccctgaaaa gattatcgag ctgtatgcgg agtgcatcag   1200
gctctttcac tccatcgaca tatcggattg tccctatacg aatagcttag acagccgctt   1260
agccgaattg gattacttac tgaataacga tctggccgat gtggattgcg aaaactggga   1320
agaagacact ccatttaaag atccgcgcga gctgtatgat ttttttaaaga cggaaaagcc   1380
cgaagaggaa cttgtctttt cccacggcga cctgggagac agcaacatct tgtgaaaga   1440
tggcaaagta agtggcttta ttgatcttgg gagaagcggc agggcggaca gtggtatga   1500
cattgccttc tgcgtccggt cgatcaggga ggatatcggg gaagaacagt atgtcgagct   1560
attttttgac ttactgggga tcaagcctga ttgggagaaa ataaaatatt atattttact   1620
ggatgaattg ttttagtacc tagatgtggc gcaacgatgc cggcgacaag caggagcgca   1680
ccgacttctt ccgcatcaag tgttttggct ctcaggccga ggcccacggc aagtatttgg   1740
gcaagggtc gctggtattc gtgcagggca agattcggaa taccaagtac gagaaggacg   1800
gccagacggt ctacgggacc gacttcattg ccgataaggt ggattatctg acaccaagg   1860
caccaggcgg gtcaaatcag gaataagggc acattgcccc ggcgtgagtc ggggcaatcc   1920
cgcaaggagg gtgaatgaat cggacgtttg accggaaggc atacaggcaa gaactgatcg   1980
acgcggggtt ttccgccgag gatgccgaaa ccatcgcaag ccgcaccgtc atgcgtgcgc   2040
cccgcgaaac cttccagtcc gtcggctcga tggtccagca agctacggcc aagatcgagc   2100
gcgacagcgt gcaactggct cccctgccc tgcccgcgcc atcggccgcc gtggagcgtt   2160
cgcgtcgtct cgaacaggag gcggcaggtt tggcgaagtc gatgaccatc gacacgcgag   2220
gaactatgac gaccaagaag cgaaaaaccg ccggcgagga cctggcaaaa caggtcagcg   2280
aggccaagca ggccgcgttg ctgaaacaca cgaagcagca gatcaaggaa atgcagcttt   2340
ccttgttcga tattgcgccg tggccggaca cgatgcgagc gatgccaaac gacacggccc   2400
gctctgccct gttcaccacg cgcaacaaga aaatcccgcg cgaggcgctg caaaacaagg   2460
tcattttcca cgtcaacaag gacgtgaaga tcacctacac cggcgtcgag ctgcgggccg   2520
acgatgacga actggtgtgg cagcaggtgt tggagtacgc gaagcgcacc cctatcggcg   2580
agccgatcac cttcacgttc tacgagcttt gccaggacct gggctggtcg atcaatggcc   2640
ggtattacac gaaggccgag gaatgcctgt cgcgcctaca ggcgacggcg atgggcttca   2700
cgtccgaccg cgttgggcac ctggaatcgg tgtcgctgct gcaccgcttc cgcgtcctgg   2760
accgtggcaa gaaaacgtcc cgttgccagg tcctgatcga cgaggaaatc gtcgtgctgt   2820
ttgctggcga ccactacacg aaattcatat gggagaagta ccgcaagctg tcgccgacgg   2880
cccgacggat gttcgactat ttcagctcgc accgggagcc gtaccgctc aagctggaaa   2940
ccttccgcct catgtgcgga tcggattcca cccgcgtgaa gaagtggcgc gagcaggtcg   3000
gcgaagcctg cgaagagttg cgaggcagcg gcctggtgga acacgcctgg gtcaatgatg   3060
acctggtgca ttgcaaacgc tagggccttg tggggtcagt tccggctggg ggttcagcca   3120
gcgctttact gagatctggg gaaccctgtg gttggcatgc acatacaaat ggacgaacgg   3180
ataaaccttt tcacgcccctt ttaaatatcc gattattcta ataaacgctc ttttctctta   3240
ggtttacccg ccaatatatc ctgtcaaaca ctgatagttt aaactgaagg cgggaaacga   3300
```

```
caatctgatc atgagcggag aattaaggga gtcacgttat gaccccgcc gatgacgcgg    3360 gacaagccgt tttacgtttg gaactgacag aaccgcaacg ttgaaggagc cactcagccg    3420
cgggtttctg gagtttaatg agctaagcac atacgtcaga aaccattatt gcgcgttcaa    3480
aagtcgccta aggtcactat cagctagcaa atatttcttg tcaaaaatgc tccactgacg    3540
ttccataaat tcccctcggt atccaattag agtctcatat tcactctcaa tccaaataat    3600
ctgcaccgga tctggatcgt ttcgcatgat tgaacaagat ggattgcacg caggttctcc    3660
ggccgcttgg gtggagaggc tattcggcta tgactgggca caacagacaa tcggctgctc    3720
tgatgccgcc gtgttccggc tgtcagcgca ggggcgcccg gttctttttg tcaagaccga    3780
cctgtccggt gccctgaatg aactgcagga cgaggcagcg cggctatcgt ggctggccac    3840
gacgggcgtt ccttgcgcag ctgtgctcga cgttgtcact gaagcgggaa gggactggct    3900
gctattgggc gaagtgccgg ggcaggatct cctgtcatct caccttgctc ctgccgagaa    3960
agtatccatc atggctgatg caatgcgcg gctgcatacg cttgatccgg ctacctgccc    4020
attcgaccac caagcgaaac atcgcatcga gcgagcacgt actcggatgg aagccggtct    4080
tgtcgatcag gatgatctgg acgaagagca tcagggctc gcgccagccg aactgttcgc    4140
caggctcaag gcgcgcatgc ccgacggcga tgatctcgtc gtgacccatg gcgatgcctg    4200
cttgccgaat atcatggtgg aaaatggccg cttttctgga ttcatcgact gtggccggct    4260
gggtgtggcg gaccgctatc aggacatagc gttggctacc cgtgatattg ctgaagagct    4320
tggcggcgaa tgggctgacc gcttcctcgt gctttacggt atcgccgctc ccgattcgca    4380
gcgcatcgcc ttctatcgcc ttcttgacga gttcttctga gcgggactct ggggttcgaa    4440
atgaccgacc aagcgacgcc caacctgcca tcacgagatt tcgattccac cgccgccttc    4500
tatgaaaggt tgggcttcgg aatcgttttc cgggacgccg gctggatgat cctccagcgc    4560
ggggatctca tgctggagtt cttcgcccac gggatctctg cggaacaggc ggtcaaggt    4620 gccgatatca ttacgacagc aacggccgac aagcacaacg ccacgatcct gagcgacaat    4680
atgatcgggc ccggcgtcca catcaacggc gtcggcggcg actgcccagg caagaccgag    4740
atgcaccgcg atatcttgct gcgttcggat attttcgtgg agttcccgcc acagacccgg    4800 atgatcccg atcgttcaaa catttggcaa taaagtttct taagattgaa tcctgttgcc    4860
ggtcttgcga tgattatcat ataatttctg ttgaattacg ttaagcatgt aataattaac    4920
atgtaatgca tgacgttatt tatgagatgg gttttatga ttagagtccc gcaattatac    4980
atttaatacg cgatagaaaa caaaatatag cgcgcaaact aggataaatt atcgcgcgcg    5040
gtgtcatcta tgttactaga tcgggccaat acgcaaaccg cctctccccg cgcgttggcc    5100
gattcattaa tgcagctggc acgacaggtt cccgactgg aaagcgggca gtgagcgcaa    5160
cgcaattaat gtgagttagc tcactcatta ggcaccccag gctttacact ttatgcttcc    5220
ggctcgtatg ttgtgtggaa ttgtgagcgg ataacaattt cacacaggaa acagctatga    5280
ccatgattac gccaagcttg catgcctgca ggtcactgga ttttggtttt aggaattaga    5340
aattttattg atagaagtat tttacaaata caaatacata ctaagggttt cttatatgct    5400
caacacatga gcgaaaccct ataagaaccc taattccctt atctgggaac tactcacaca    5460
ttattctgga gaaaatagag agagatagat tgtagagag agactggtga tttttgcgga    5520
ctctatcgac ggatcgggct agagttcgtc tttggaacca ttcagatcct cttctgagat    5580 gagttttgt tctgcggcca aatggtgatg gtggtgatgc gcggccgcgg aatccatatg    5640
```

```
ctgtctttcg aacttagctg ctgctgtctc tttgctagct gaaccacctc cacctctttc    5700
tccaataagt ttcttgatac gagcgatctc gttctcgata tgataaatct tggaaagaat    5760
ttcctcgatc ttatcctcga tctgcttcat tctcttgggc ccctccaatt tcacccctga    5820
aatttcttcc cgtttcaatt tggcctcttc agaatactgg ggataatcat atgtgccatt    5880
cctcacgctc tccatgcact cattatcgca tttgtgataa aactcaaaac agccattccc    5940
aagctctttg gcattatccc taagctgaag cctgactttg tcgtaaagat ttttcacatt    6000
gctatcgtga aagtccaaag tacgctcatt ttccataagc accaacaatt cagcattata    6060
tgtccacaca tcgagaaacc cgtcctccat tttcttattg agattttcaa ttcgacgttc    6120
aagattattg aattccctgc cgactgcttc aaactgagta ttcattttat caataataga    6180
attcactttg ttagtgaccc catcaatagc tttctgagtt gattctttat cagcagcata    6240
acctgaaccc tgttcatttg agtgatgata accataccaa ccatcaacca taccctgcca    6300
accaccttcg ataaaaccag caatagcacc aaacaaacct cgacgttccc tctgcgggct    6360
atttcgtaaa ccagtagcga gaaccaaacg attagacttc acatacttcg gacattctcc    6420
aatggtcagg gggtgaatat tatgaaaagg catgcttgaa ttaatagctc ccataggggt    6480
ttggcacttg gtattacaat taccgtactc cagctcgctt ttcataatgg ttgagtcgcc    6540
tttcttgact atcttgtagg cgtactcagg agcaatgaaa ttcccattgg actcaaaatt    6600
aattgcgtca ttaggtttga gtatggtcca aaagaattcc attcttccgc tttgaccatt    6660
aaccttactt ctcgtagcaa ttcttggaac aagtctttgg ttgagagtgg atgttccaac    6720
ggatatgtat gtagttgggt tttgatagag ctttgtttgt tctgctgcat cgtttggatg    6780
atgaattccc catagaacaa gcagatcctc ttggttcgtg ttgttgtaac tcctctttat    6840
ggttgggtat gtggagttct tctttatcaa ccacacaacg tttctgaaga atgaagattt    6900
tccttgatat ggacatgcag aactaactcc aagagatgct tcatgactag gccaagagga    6960
cttcggtatg atctgaatct tctcgaagtg gttaattcta gatagcagat gcttaagctc    7020
ttcgtaatcg ttgaaatctc cagggtaaca caaatcgtta actgggtttg ccttttcaac    7080
gatgtaactc cattctggaa cgttgataaa ctcatcacac ataggatttc ctaacaacca    7140
tccagcaacg gaacaatctc taaggatcaa aggcttaact ccatctaggt cacatagctt    7200
tccgttatga gtcttctcaa ggatatcttg tgcatgtgta accgttacgt tcttctccat    7260
gattgtgtct acttgctctg tactgttatt agcatggtaa ccgatgcaga tttggtcgga    7320
tcctgctaaa catgtgcttg taaagagaag caaggaaagt gaaagcaaag atagaaaagg    7380
tttggaagcc atggttcccg gccgggtcag atcctctaga gtcgatcgag gtcctctcca    7440
aatgaaatga acttccttat atagaggaag ggtcttgcga aggatagtgg gattgtgcgt    7500
catcccttac gtcagtggag atatcacatc aatccacttg ctttgaagac gtggttggaa    7560
cgtcttcttt ttccacgatg ttcctcgtgg gtggggtcc atctttggga ccactgtcgg    7620
tagaggcatt cttgaacgat agcctttcct ttatcgcaat gatggcattt gtagaagcca    7680
tcttcctttt ctactgtcct ttcgatgaag tgacagatag ctgggcaatg gaatccgagg    7740
aggtttcccg atattcccct ttgttgaaaa gtctcaatag ccctctggtc ttctgagact    7800
gtatctttga tattcttgga gtagacgaga gtgtcgtgct ccaccatgtt gacctgcagg    7860
catgcaagct tatcgatacc gtcgacctcg agggggggcc cggtaccaaa accaccccag    7920
tacattaaaa acgtccgcaa tgtgttatta agttgtctaa gcgtcaattt gtttacacca    7980
caatatatcc tgccaccagc cagccaacag ctccccgacc ggcagctcgg cacaaaatca    8040
```

```
ccactcgata caggcagccc atcagtccac taga                                  8074
```

<210> SEQ ID NO 29
<211> LENGTH: 6733
<212> TYPE: DNA
<213> ORGANISM: Artificial Sequence
<220> FEATURE:
<223> OTHER INFORMATION: pCB_S-protein-tail piece

<400> SEQUENCE: 29

```
cgctcaccgg gctggttgcc ctcgccgctg ggctggcggc cgtctatggc cctgcaaacg    60
cgccagaaac gccgtcgaag ccgtgtgcga gacaccgcgg ccgccggcgt tgtggatacc   120
tcgcggaaaa cttggccctc actgacagat gaggggcgga cgttgacact tgaggggccg   180
actcacccgg cgcggcgttg acagatgagg ggcaggctcg atttcggccg gcgacgtgga   240
gctggccagc ctcgcaaatc ggcgaaaacg cctgatttta cgcgagtttc ccacagatga   300
tgtggacaag cctggggata agtgccctgc ggtattgaca cttgaggggc gcgactactg   360
acagatgagg ggcgcgatcc ttgacacttg agggcagag tgctgacaga tgaggggcgc   420
acctattgac atttgagggg ctgtccacag gcagaaaatc cagcatttgc aagggtttcc   480
gcccgttttt cggccaccgc taacctgtct tttaacctgc ttttaaacca atatttataa   540
accttgtttt taaccagggc tgcgcccgt gcgcgtgacc gcgcacgccg aaggggggtg   600
ccccccttc tcgaacccctc ccggcccgct ctcgagttgg cagcatcacc cataattgtg   660
gtttcaaaat cggctccgtc gatactatgt tatacgccaa cttttgaaaac aactttgaaa   720
aagctgtttt ctggtattta aggttttaga atgcaaggaa cagtgaattg gagttcgtct   780
tgttataatt agcttcttgg ggtatcttta aatactgtag aaaagaggaa ggaaataata   840
aatggctaaa atgagaatat caccggaatt gaaaaaactg atcgaaaaat accgctgcgt   900
aaaagatacg gaaggaatgt ctcctgctaa ggtatataag ctggtgggag aaaatgaaaa   960
cctatattta aaaatgacgg acagccggta taaagggacc acctatgatg tggaacggga  1020
aaaggacatg atgctatggc tggaaggaaa gctgcctgtt ccaaaggtcc tgcactttga  1080
acggcatgat ggctggagca atctgctcat gagtgaggcc gatggcgtcc tttgctcgga  1140
agagtatgaa gatgaacaaa gccctgaaaa gattatcgag ctgtatgcgg agtgcatcag  1200
gctctttcac tccatcgaca tatcggattg tcctatacg aatagcttag acagccgctt  1260
agccgaattg gattacttac tgaataacga tctggccgat gtggattgcg aaaactggga  1320
agaagacact ccatttaaag atccgcgcga gctgtatgat ttttaaaga cggaaaagcc  1380
cgaagaggaa cttgtctttt cccacggcga cctgggagac agcaacatct tgtgaaaga  1440
tggcaaagta agtggcttta ttgatcttgg agaagcggc agggcggaca gtggtatga  1500
cattgccttc tgcgtccggt cgatcaggga ggatatcggg gaagaacagt atgtcgagct  1560
atttttgac ttactgggga tcaagcctga ttggagaaa ataaaatatt atatttact  1620
ggatgaattg ttttagtacc tagatgtggc gcaacgatgc cggcgacaag caggagcgca  1680
ccgacttctt ccgcatcaag tgttttggct ctcaggccga ggcccacggc aagtatttgg  1740
gcaagggtc gctggtattc gtgcagggca agattcggaa taccaagtac gagaaggacg  1800
gccagacggt ctacgggacc gacttcattg ccgataaggt ggattatctg gacaccaagg  1860
caccaggcgg gtcaaatcag gaataagggc acattgcccc ggcgtgagtc ggggcaatcc  1920
cgcaaggagg gtgaatgaat cggacgtttg accggaaggc atacaggcaa gaactgatcg  1980
```

-continued

```
acgcggggtt ttccgccgag gatgccgaaa ccatcgcaag ccgcaccgtc atgcgtgcgc    2040
cccgcgaaac cttccagtcc gtcggctcga tggtccagca agctacggcc aagatcgagc    2100
gcgacagcgt gcaactggct cccccctgccc tgcccgcgcc atcggccgcc gtggagcgtt    2160
cgcgtcgtct cgaacaggag gcggcaggtt tggcgaagtc gatgaccatc gacacgcgag    2220
gaactatgac gaccaagaag cgaaaaaccg ccggcgagga cctggcaaaa caggtcagcg    2280
aggccaagca ggccgcgttg ctgaaacaca cgaagcagca gatcaaggaa atgcagcttt    2340
ccttgttcga tattgcgccg tggccggaca cgatgcgagc gatgccaaac gacacggccc    2400
gctctgccct gttcaccacg cgcaacaaga aaatcccgcg cgaggcgctg caaaacaagg    2460
tcattttcca cgtcaacaag gacgtgaaga tcacctacac cggcgtcgag ctgcgggccg    2520
acgatgacga actggtgtgg cagcaggtgt tggagtacgc gaagcgcacc cctatcggcg    2580
agccgatcac cttcacgttc tacgagcttt gccaggacct gggctggtcg atcaatggcc    2640
ggtattacac gaaggccgag gaatgcctgt cgcgcctaca ggcgacggcg atgggcttca    2700
cgtccgaccg cgttgggcac ctggaatcgg tgtcgctgct gcaccgcttc cgcgtcctgg    2760
accgtggcaa gaaaacgtcc cgttgccagg tcctgatcga cgaggaaatc gtcgtgctgt    2820 tgctggcga ccactacacg aaattcatat gggagaagta ccgcaagctg tcgccgacgg    2880
cccgacggat gttcgactat ttcagctcgc accgggagcc gtaccgcctc aagctggaaa    2940
ccttccgcct catgtgcgga tcggattcca cccgcgtgaa gaagtggcgc gagcaggtcg    3000
gcgaagcctg cgaagagttg cgaggcagcg gcctggtgga acacgcctgg gtcaatgatg    3060
acctggtgca ttgcaaacgc tagggccttg tggggtcagt tccggctggg ggttcagcca    3120
gcgctttact gagatctggg gaaccctgtg gttggcatgc acatacaaat ggacgaacgg    3180 ataaacctttt tcacgcccttt ttaaatatcc gattattcta ataaacgctc ttttctctta    3240
ggtttacccg ccaatatatc ctgtcaaaca ctgatagttt aaactgaagg cgggaaacga    3300
caatctgatc atgagcggag aattaaggga gtcacgttat gacccccgcc gatgacgcgg    3360
gacaagccgt tttacgtttg gaactgacag aaccgcaacg ttgaaggagc cactcagccg    3420
cgggtttctg gagtttaatg agctaagcac atacgtcaga aaccattatt gcgcgttcaa    3480
aagtcgccta aggtcactat cagctagcaa atatttcttg tcaaaaatgc tccactgacg    3540
ttccataaat tcccctcggt atccaattag agtctcatat tcactctcaa tccaaaataat    3600 ctgcaccgga tctggatcgt ttcgcatgat tgaacaagat ggattgcacg caggttctcc    3660
ggccgcttgg gtggagaggc tattcggcta tgactgggca caacagacaa tcggctgctc    3720
tgatgccgcc gtgttccggc tgtcagcgca ggggcgcccg gttcttttttg tcaagaccga    3780 cctgtccggt gccctgaatg aactgcagga cgaggcagcg cggctatcgt ggctggccac    3840
gacgggcgtt ccttgcgcag ctgtgctcga cgttgtcact gaagcgggaa gggactggct    3900
gctattgggc gaagtgccgg ggcaggatct cctgtcatct caccttgctc ctgccgagaa    3960
agtatccatc atggctgatg caatgcggcg gctgcatacg cttgatccgg ctacctgccc    4020
attcgaccac caagcgaaac atcgcatcga gcgagcacgt actcggatgg aagccggtct    4080
tgtcgatcag gatgatctgg acgaagagca tcagggcctc gcgccagccg aactgttcgc    4140
caggctcaag gcgcgcatgc ccgacggcga tgatctcgtc gtgacccatg gcgatgcctg    4200
cttgccgaat atcatggtgg aaaatggccg cttttctgga ttcatcgact gtggccggct    4260
gggtgtggcg gaccgctatc aggacatagc gttggctacc cgtgatattg ctgaagagct    4320
tggcggcgaa tgggctgacc gcttcctcgt gctttacggt atcgccgctc ccgattcgca    4380
```

```
gcgcatcgcc ttctatcgcc ttcttgacga gttcttctga gcgggactct ggggttcgaa      4440
atgaccgacc aagcgacgcc caacctgcca tcacgagatt tcgattccac cgccgccttc      4500
tatgaaaggt tgggcttcgg aatcgttttc cgggacgccg gctggatgat cctccagcgc      4560
ggggatctca tgctggagtt cttcgcccac gggatctctg cggaacaggc ggtcgaaggt      4620
gccgatatca ttacgacagc aacggccgac aagcacaacg ccacgatcct gagcgacaat      4680
atgatcgggc ccggcgtcca catcaacggc gtcggcggcg actgcccagg caagaccgag      4740
atgcaccgcg atatcttgct gcgttcggat attttcgtgg agttcccgcc acagacccgg      4800
atgatccccg atcgttcaaa catttggcaa taaagtttct taagattgaa tcctgttgcc      4860
ggtcttgcga tgattatcat ataatttctg ttgaattacg ttaagcatgt aataattaac      4920
atgtaatgca tgacgttatt tatgagatgg gttttttatga ttagagtccc gcaattatac      4980
atttaatacg cgatagaaaa caaaatatag cgcgcaaact aggataaatt atcgcgcgcg      5040
gtgtcatcta tgttactaga tcgggccaat acgcaaaccg cctctccccg cgcgttggcc      5100
gattcattaa tgcagctggc acgacaggtt tcccgactgg aaagcgggca gtgagcgcaa      5160
cgcaattaat gtgagttagc tcactcatta ggcaccccag gctttacact ttatgcttcc      5220
ggctcgtatg ttgtgtggaa ttgtgagcgg ataacaattt cacacaggaa acagctatga      5280
ccatgattac gccaagcttg agctcctgca ggtcactgga ttttggtttt aggaattaga      5340
aattttattg atagaagtat tttacaaata caaatacata ctaagggttt cttatatgct      5400
caacacatga gcgaaaccct ataagaaccc taattccctt atctgggaac tactcacaca      5460
ttattctgga gaaaatagag agagatagat ttgtagagag agactggtga tttttgcgga      5520
ctctatcgac ggatcgggct agagttcgtc tttggaacca ttcagatcct cttctgagat      5580 gagttttgt tctgcggccg cgtaacaagt cccgccggta tcggacataa tgagggaaac      5640
attatacaat gtcggtttgc tagcaacaga ggcgtcaaaa tgaaccggca catagggatt      5700
tccttcgcag gcgacaatta tgtgtttatt agcttgagta gttttataag cgcaatttgg      5760
atatttgcta gacccagttt ctcggcaatc ggtgatagac atggtggagt agctttggta      5820
gcaattcgtt tgaccattct tacaagccac attcttttgt gaacaaacag cctgaacatc      5880
tgccaatgac tcgtgacaa atgtgtttac aggcttacac ctgtcctttg taaggttacg      5940
tgacttcatc atctggttac agtagttact agaactggat cctgctaaac atgtgcttgt      6000
aaagagaagc aaggaaagtg aaagcaaaga tagaaaaggt ttggaagcca tggttcccgg      6060
ccgggtcaga tcctctagag tcgatcgagg tcctctccaa atgaaatgaa cttccttata      6120
tagaggaagg gtcttgcgaa ggatagtggg attgtgcgtc atcccttacg tcagtggaga      6180
tatcacatca atccacttgc tttgaagacg tggttggaac gtcttctttt tccacgatgt      6240
tcctcgtggg tgggggtcca tctttgggac cactgtcggt agaggcattc ttgaacgata      6300
gcctttcctt tatcgcaatg atggcatttg tagaagccat cttcctttc tactgtcctt       6360 tcgatgaagt gacagatagc tgggcaatgg aatccgagga ggtttcccga tattacccct      6420
tgttgaaaag tctcaatagc cctctggtct tctgagactg tatctttgat attcttggag      6480
tagacgagag tgtcgtgctc caccatgttg acctgcaggt cgacaagctt atcgataccg      6540
tcgacctcga ggggggggccc ggtaccaaaa ccaccccagt acattaaaaa cgtccgcaat      6600
gtgttattaa gttgtctaag cgtcaatttg tttacaccac aatatatcct gccaccagcc      6660
agccaacagc tccccgaccg gcagctcggc acaaaatcac cactcgatac aggcagccca      6720
```
tcagtccact aga                                                            6733

<210> SEQ ID NO 30
<211> LENGTH: 19
<212> TYPE: PRT
<213> ORGANISM: Suncus murinus

<400> SEQUENCE: 30

Lys Pro Thr Leu Tyr Asn Val Ser Leu Val Leu Ser Asp Thr Ala Ser
1               5                   10                  15

Thr Cys Tyr

<210> SEQ ID NO 31
<211> LENGTH: 19
<212> TYPE: PRT
<213> ORGANISM: Bos taurus

<400> SEQUENCE: 31

Lys Pro Thr Leu Tyr Asn Val Ser Leu Val Leu Ser Asp Thr Ala Ser
1               5                   10                  15

Thr Cys Tyr

<210> SEQ ID NO 32
<211> LENGTH: 19
<212> TYPE: PRT
<213> ORGANISM: Trachemys scripta elegans

<400> SEQUENCE: 32

Lys Pro Thr Ala Val Asn Val Ser Val Ile Leu Ser Asp Thr Asp Ile
1               5                   10                  15

Thr Cys Tyr

<210> SEQ ID NO 33
<211> LENGTH: 19
<212> TYPE: PRT
<213> ORGANISM: Mesocricetus auratus

<400> SEQUENCE: 33

Lys Pro Thr Leu Tyr Asn Val Ser Leu Ile Met Ser Asp Ala Gly Gly
1               5                   10                  15

Thr Cys Tyr

<210> SEQ ID NO 34
<211> LENGTH: 19
<212> TYPE: PRT
<213> ORGANISM: Homo sapiens

<400> SEQUENCE: 34

Lys Pro Thr His Val Asn Val Ser Val Val Met Ala Glu Val Asp Gly
1               5                   10                  15

Thr Cys Tyr

<210> SEQ ID NO 35
<211> LENGTH: 567
<212> TYPE: PRT
<213> ORGANISM: Avian influenza virus

<400> SEQUENCE: 35

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val

-continued

```
                20                  25                  30
Asp Thr Ile Met Glu Lys Asn Val Thr Val Thr His Ala Gln Asp Ile
             35                  40                  45
Leu Glu Lys Thr His Asn Gly Lys Leu Cys Asp Leu Asp Gly Val Lys
 50                  55                  60
Pro Leu Ile Leu Arg Asp Cys Ser Val Ala Gly Trp Leu Leu Gly Asn
 65                  70                  75                  80
Pro Met Cys Asp Glu Phe Ile Asn Val Pro Glu Trp Ser Tyr Ile Val
                 85                  90                  95
Glu Lys Ala Asn Pro Val Asn Asp Leu Cys Tyr Pro Gly Asp Phe Asn
            100                 105                 110
Asp Tyr Glu Glu Leu Lys His Leu Leu Ser Arg Ile Asn His Phe Glu
            115                 120                 125
Lys Ile Gln Ile Ile Pro Lys Ser Ser Trp Ser His Glu Ala Ser
            130                 135                 140
Leu Gly Val Ser Ser Ala Cys Pro Tyr Gln Gly Lys Ser Ser Phe Phe
145                 150                 155                 160
Arg Asn Val Val Trp Leu Ile Lys Lys Asn Ser Thr Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Lys Leu Tyr Gln
            195                 200                 205
Asn Pro Thr Thr Tyr Ile Ser Val Gly Thr Ser Thr Leu Asn Gln Arg
            210                 215                 220
Leu Val Pro Arg Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Thr Ile Met Lys Ser Glu Leu Glu Tyr Gly
            275                 280                 285
Asn Cys Asn Thr Lys Cys Gln Thr Pro Met Gly Ala Ile Asn Ser Ser
            290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Arg Gly Leu Phe Gly Ala Ile Ala
            340                 345                 350
Gly Phe Ile Glu Gly Gly Trp Gln Gly Met Val Asp Gly Trp Tyr Gly
            355                 360                 365
Tyr His His Ser Asn Glu Gln Gly Ser Gly Tyr Ala Ala Asp Lys Glu
            370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                405                 410                 415
Asn Leu Glu Arg Arg Ile Glu Asn Leu Asn Lys Lys Met Glu Asp Gly
            420                 425                 430
Phe Leu Asp Val Trp Thr Tyr Asn Ala Glu Leu Leu Val Leu Met Glu
            435                 440                 445
```

```
Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Lys
                500                 505                 510

Leu Lys Arg Glu Glu Ile Ser Gly Val Lys Leu Glu Ser Ile Gly Ile
            515                 520                 525

Tyr Gln Ile Leu Thr Ile Tyr Ser Thr Val Ala Ser Ser Leu Ala Leu
530                 535                 540

Ala Ile Met Val Ala Gly Leu Ser Leu Trp Met Cys Ser Asn Gly Ser
545                 550                 555                 560

Leu Gln Cys Arg Ile Cys Ile
            565

<210> SEQ ID NO 36
<211> LENGTH: 567
<212> TYPE: PRT
<213> ORGANISM: Avian Influenza virus

<400> SEQUENCE: 36

Met Glu Lys Ile Val Leu Leu Phe Ala Thr Ile Ser Leu Val Lys Ser
1               5                   10                  15

Asp His Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Leu Cys Asp Glu Phe Ile Asn Val Pro Glu Trp Ser Tyr Ile Val
                85                  90                  95

Glu Lys Pro Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asp Ser Trp Ser Asn His Glu Ala Ser
    130                 135                 140

Leu Gly Val Ser Ala Ala Cys Ser Tyr Gln Gly Asn Ser Ser Phe Phe
145                 150                 155                 160

Arg Asn Val Val Trp Leu Ile Lys Lys Asp Asn Ala Tyr Pro Thr Ile
                165                 170                 175

Lys Lys Gly Tyr Asn Asn Thr Asn Arg Glu Asp Leu Leu Ile Leu Trp
            180                 185                 190

Gly Ile His His Pro Asn Asp Glu Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Ile Asn Gly Gln Ser Gly
225                 230                 235                 240

Arg Ile Asp Phe Phe Trp Thr Ile Leu Lys Pro Asn Asp Ala Ile His
```

```
                245                 250                 255
Phe Glu Ser Asn Gly Asn Phe Ile Ala Pro Glu Tyr Ala Tyr Lys Ile
            260                 265                 270

Val Lys Lys Gly Asp Ser Thr Ile Met Arg Ser Glu Val Glu Tyr Gly
        275                 280                 285

Asn Cys Asn Thr Arg Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
            325                 330                 335

Pro Gln Arg Glu Arg Arg Lys Arg Gly Leu Phe Gly Ala Ile Ala
        340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
            405                 410                 415

Asn Leu Glu Arg Arg Ile Glu Asn Leu Asn Lys Lys Met Glu Asp Gly
        420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
        450                 455                 460

Asp Lys Val Arg Leu Gln Leu Lys Asp Asn Ala Lys Glu Leu Gly Asn
465                 470                 475                 480

Gly Cys Phe Glu Phe Tyr His Lys Cys Asn Asn Glu Cys Met Glu Ser
            485                 490                 495

Val Arg Asn Gly Thr Tyr Asp Tyr Pro Gln Tyr Ser Glu Glu Ala Arg
        500                 505                 510

Leu Lys Arg Glu Glu Ile Ser Gly Val Lys Leu Glu Ser Ile Gly Ile
        515                 520                 525

Tyr Gln Ile Leu Ser Ile Tyr Ser Thr Val Ala Ser Ser Leu Ala Leu
        530                 535                 540

Ala Ile Met Met Ala Gly Leu Ser Leu Trp Met Cys Ser Asn Gly Ser
545                 550                 555                 560

Leu Gln Cys Arg Ile Cys Ile
            565

<210> SEQ ID NO 37
<211> LENGTH: 238
<212> TYPE: PRT
<213> ORGANISM: Artificial Sequence
<220> FEATURE:
<223> OTHER INFORMATION: enhanced green fluorescent protein (eGFP)

<400> SEQUENCE: 37

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
```

```
                 35                  40                  45
Thr Thr Gly Lys Leu Pro Val Pro Trp Pro Thr Leu Val Thr Thr Leu
         50                  55                  60

Thr Tyr Gly Val Gln Cys Phe Ser Arg Tyr Pro Asp His Met Lys Gln
65                   70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
                115                 120                 125

Asp Phe Lys Glu Asp Gly Asn Ile Leu Gly His Lys Leu Glu Tyr Asn
                130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
                210                 215                 220

Thr Ala Ala Gly Ile Thr Leu Gly Met Asp Glu Leu Tyr Lys
225                 230                 235
```

OLIGOMERIC VACCINES FROM PLANTS BY S-TAG-S-PROTEIN FUSIONS

RELATED APPLICATIONS

This application is a national stage filing under 35 U.S.C. 371 of international patent application number PCT/EP2017/084136, filed Dec. 21, 2017, which claims the benefit of European application number EP16206231.9, filed Dec. 22, 2016, each of which is herein incorporated by reference in its entirety.

The present invention relates to a method for production of an oligomeric protein in eukaryotic cells by co-expression of two fusion proteins in eukaryotic cells, the oligomeric protein and its use in vaccines.

STATE OF THE ART

Influenza A viruses, negative-stranded enveloped orthomyxoviruses, belong to the most serious respiratory pathogens. They cause severe and potentially fatal illnesses (Cox et al. 2004). Highly pathogenic avian influenza viruses are expected to cause the next global pandemic threat because of the easy spreading by avian hosts and their capability to directly infect humans (Yen et Webster 2009). Therefore, the development of an effective and cheap vaccination strategy is an upcoming demand.

In the focus of research are subunit vaccines from plants. Topp et al. disclose the production of proteins recombinantly in plants (Topp et al. 2016). A recently developed strategy is the production of virus-like particle based vaccines in tobacco species *N. benthamiana* by cloning a hemagglutinin gene into a well-characterized vector and transient expression (Landry et al. 2010, D'Aoust et al. 2008). Disadvantageously, this strategy includes downstream processing steps as several filtrations, diafiltrations, continuous flow centrifugations and tangential flow filtration, or, alternatively, chromatographic methods.

Alternatively, trimeric hemagglutinin was produced transiently in the endoplasmic reticulum (ER) of *N. benthamiana* leaf cells to circumvent constraints as high down-stream cost and low expression levels of the virus-like particles (Phan et al. 2013). For the trimerisation hemagglutinin was C terminally fused with the trimeric motif GCN4-pII (Harbury et al. 1993).

Czajkowsky et al. disclose the use of Fc fusion proteins as vaccines (Czajkowsky et al. 2012), wherein the Fc fusions increase the therapeutic activity of antigens by the increase of the plasma half-life, the increase of the interactions with the Fc receptor and the increase of the solubility and stability. Louveiro et al. describe an influenza vaccine based on hemagglutinin-Fc fusion proteins (human H1, H3 influenza viruses and avian H5 influenza viruses) (Loureiro et al. 2011).

U.S. Pat. No. 7,067,110 B1 discloses Fc-fusion proteins for enhancing the immunogenicity of protein and peptide antigens, wherein the antigen is fused to the immunoglobulin heavy chain constant region ($CH_2$, $CH_3$, $CH_4$). Furthermore, the vaccine comprises adjuvants for the enhancement or modulation of a particular immune response, preferred human cytokines. Antigens are selected from prostate-specific membrane antigen, the ectodomain of a cytokine receptor, a viral protein or a tumor-specific protein.

Alternatively, the purification of antigens for the use in vaccines is described by using antigen fusion proteins with S-Tag. U.S. Pat. No. 7,311,918 B2 discloses a rotavirus subunit vaccine comprising a recombinant rotavirus fusion protein with a fusion partner selected from maltose binding protein, poly-histidine residues, S-Tag, glutathione-S-transferase etc., which prevents the rotavirus fusion protein from complex formation and facilitates purification. US 2013/0164296 A1 discloses fusion proteins linked with for example maltose binding protein, S-Tag or glutathione-S-transferase as subunit vaccine immunogens, wherein the fusion protein partner may prevent the assembly of viral fusion protein into multimeric forms. Asai et al. disclose the use of the specific interaction between S-Tag, the amino-terminal 15-amino acid peptide derived from human ribonuclease 1 (human S-Tag), and S-protein, residues 21 to 124 of the human ribonuclease 1, for the site-specific conjugation of an enzyme to an antibody for targeted drug delivery for the treatment of cancer (Asai et al. 2005).

In contrast, US 2013/0039942 A1 discloses compositions and methods for self-adjuvanting vaccines against microbes and tumors, wherein a multimerization-intracellular signaling cassette is inserted in a virus or vector.

Wei et al. (Wei et al. 2008) describe the comparison of various forms of recombinant hemagglutinin (HA) proteins, monomeric, trimeric and oligomeric H5N1 HA proteins, for their potential efficacy as vaccines. The recombinant monomeric, trimeric and oligomeric H5N1 HA proteins were expressed in *Trichoplusia ni* (Hi5) cells, as a high-molecular-weight oligomer (1,321 kDa) and a trimer (214 kDa), and in human embryonic kidney cell line 293F. The high-molecular-weight oligomer of HA elicited the strongest antibody response, followed by the trimeric HA and the monomeric HA showed minimal efficacy.

Thus, there remains a need for a method for production of vaccines with improved immunogenicity in terms of inducing potentially neutralizing antibodies, low down-stream cost and high expression levels.

OBJECT OF THE PRESENT INVENTION

The invention has the object of finding an effective and fast vaccination strategy as well as an easy and fast method for producing an oligomeric protein, preferably used as vaccine.

CHARACTER OF THE PRESENT INVENTION

The objective of the invention is solved by a method for production of an oligomeric protein in eukaryotic cells comprising the steps
a) Co-expression of two fusion proteins in eukaryotic cells comprising
   a first fusion protein comprising a protein and an S-Tag (in the following also called protein-S-Tag fusion protein), wherein the protein is an antigen or an antigen binding unit, and
   a second fusion protein comprising a S-protein and a tail piece (tp) (in the following also called S-protein-tail piece (tp) fusion protein), wherein the tail piece (tp) is an oligopeptide derived from a heavy chain of an IgM or IgA antibody,
b) Extraction of the two fusion proteins,
wherein oligomerisation of the protein of the protein-S-Tag fusion protein takes place after co-expression in eukaryotic cells according to step a) and/or after extraction according to step b).

Advantageously, the method for production of an oligomeric protein in eukaryotic cells according to the invention is fast and inexpensive.

Where reference is made hereinabove and herein below to documents, these are incorporated insofar as is necessary.

As used herein, the term "oligomeric" refers to a molecular complex that consists of a few monomer units, wherein a few refers to 2 to 20, preferred 2 to 9. The oligomeric protein according to the invention is a homo-oligomer of the monomer unit protein-S-Tag fusion protein-S-protein-tail piece fusion protein complex. As used herein, the term "oligomerisation" refers to a process of converting a monomer or a mixture of monomers into an oligomer.

Eukaryotic cells according to the invention are cells which contain a nucleus and other organelles enclosed within membranes.

Advantageously, eukaryotic cells exhibit a protein disulfide-isomerase. As used herein, the term "protein disulfide-isomerase" refers to an enzyme in the endoplasmic reticulum in eukaryotes that catalyzes the formation and breakage of disulfide bonds between cysteine residues within proteins.

In an embodiment the eukaryotic cells are selected from plant cells or yeast cells. As used herein, the term "plant cells" refers to multicellular eukaryotes of the kingdom Plantae. As used herein, the term "yeast cells" refers to single-celled eukaryotic microorganisms of the kingdom Fungi.

In a preferred embodiment eukaryotic cells are plant cells. Advantageously, the expression in plant cells offers low production costs, safety of production, ease of scalability, low infrastructure cost and high stability and shelf life of the oligomeric protein. Furthermore advantageously, plant cells are able to provide complex, correctly folded and posttranslationally modified proteins.

In an embodiment the plant cells are cells of leaves or seeds of a plant. In an embodiment the plant cells are cells of a tobacco, soybean or pea plant. In a preferred embodiment the plant cells are leaf cells of *N. benthamiana*. Advantageously, recombinant antibodies show high accumulation and long-term stability in seeds (Fiedler and Conrad, 1995).

In a further embodiment the yeast cells are cells of *Saccharomyces cerevisiae*.

As used herein, the term "co-expression" refers to the simultaneous expression of two or more genes.

As used herein, the term "fusion protein" refers to proteins created through the joining of two or more genes that originally coded for separate proteins. Translation of this fusion gene results in a single protein with functional properties derived from each of the original proteins.

Antigens according to the invention are proteins capable of inducing an immune response in a host organism, wherein the immune system produces antibodies against the antigen.

In an embodiment the antigen is a membrane protein or surface protein of virions, preferred hemagglutinin.

In a further embodiment hemagglutinin is influenza hemagglutinin, measles hemagglutinin, parainfluenza hemagglutinin-neuraminidase or mumps hemagglutinin-neuraminidase.

In a preferred embodiment hemagglutinin is selected from human H1, H3 influenza viruses or avian H5 influenza viruses, preferably from avian H5 influenza viruses (n particular SEQ ID NO. 1, 35 or 36).

In a further embodiment the first fusion protein, wherein the protein is hemagglutinin, further comprises a trimerization domain. As used herein, the term "trimerization domain" refers to oligopeptide, which is able to oligomerise. In an embodiment the trimerization domain is derived from a basic leucine zipper domain (Harbury et al. 1993), preferred the trimerization domain comprises SEQ ID NO. 27.

A used herein "antigen binding unit" is a molecule that specifically binds an antigen with a specificity and affinity of an antibody, like an antibody, an aptamer or an artificial specific binding protein. As used herein, the term "antibodies" refers to proteins which recognize antigens via the Fab's variable region and are used to identify and neutralize pathogens such as bacteria and viruses. The fragment antigen-binding (Fab) fragment is a region on an antibody that binds to antigens. It is composed of one constant and one variable domain of each of the heavy and the light chain. Antibodies according to the invention comprise nanobodies and single chain variable fragment (scFv) antibodies and other antibody fragments that comprise at least the variable domain of a light or heavy chain of an antibody.

As used herein, the term "nanobody" refers to a single-domain antibody or an antibody fragment comprising a single monomeric variable antibody domain. A nanobody is able to bind selectively to a specific antigen. Preferably, the nanobody is a VHH antibody. As used herein, the term "VHH antibody" refers to a single monomeric variable region of a heavy chain (VH). Advantageously, nanobodies exhibit a good solubility in water, a high heat resistance, a high resistance to gastric acid and stability towards proteases compared to antibodies.

As used herein, the term "single chain variable fragment (scFv) antibodies" refers to fusion proteins of the variable regions of the heavy (VH) and light chains (VL) connected with a short linker peptide, preferably of ten to 25 amino acids.

In a further embodiment the antibody is a nanobody or a single chain variable fragment (scFv) antibody, preferred a nanobody.

In a further embodiment the antibody is an antibody that specifically binds to a pathogen or a toxin. The pathogen is preferably chosen from but not limited to bacteria, parasites and viruses. The toxin is a poisonous substance that has been secreted by living organism, like pathogenic microorganisms listed above or cells infected therewith or even higher organisms like fungi or snakes.

In an embodiment the antibody is an antibody that specifically binds to a pathogen of the gastrointestinal tract, preferred the oral cavity or the intestines; or the respiratory system.

In a preferred embodiment the antibody is an anti-shigatoxoid antibody, an anti-*Brachyspira hyodysenteriae* antibody, an anti-*Eimeria* parasites antibody or an anti-enterotoxigenic *Escherichia coli* (ETEC)-antibody.

Shigatoxoids are complex holotoxins with an $AB_5$ composition comprising an enzymatically active subunit (A) and a binding domain composed of five identical B proteins of about 7.7 kDa each that form a pentamer (Fraser et al. 1994, Fraser et al. 2004). U.S. Pat. No. 8,846,058 B2 discloses a method for the generation of shigatoxoid antibodies.

In an embodiment the anti-shigatoxoid antibody is an anti-shigatoxoid type 1 antibody or an anti-shigatoxoid type 2 antibody.

*Brachyspira hyodysenteriae* causes pig's dysentery, an illness that is responsible for essential losses in pig production worldwide (Harris et Glock 1972).

*Eimeria* is a genus of apicomplexan parasites that includes various species capable of causing the disease coccidiosis in animals, for example *E. bovis, E. zuernii*, and *E. auburnensisare*. Zimmermann et al. disclose the generation of anti-*Eimeria* scFv antibodies (Zimmermann et al. 2009).

In an embodiment the anti-*Eimeria* parasites antibody is an anti-*E. tenella* antibody, an anti-*E. acervulina* antibody, an anti-*E. brunetti* antibody or an anti-*E. papillata* antibody.

Enterotoxic *E. coli* (ETEC) is a type of *Escherichia coli* and a cause of diarrhea. Enterotoxins produced by ETEC include heat-labile enterotoxin (LT) and heat-stable enterotoxin (ST). ETEC strains exhibit on their surface F4 fimbriae, hair like appendages. Virdi et al. disclose the generation of anti-enterotoxigenic *Escherichia coli* (ETEC)-antibody or anti-F4 fimbriae antibodies, respectively (Virdi et al. 2013).

In an embodiment the anti-enterotoxigenic *Escherichia coli* (ETEC)-antibody is an anti-FaeGab antibody, an anti-FaeGac antibody or anti-FaeGad antibody.

In a preferred embodiment the antibody is an anti-shigatoxoid nanobody.

In an embodiment the S-Tag of the antigen-S-Tag fusion protein is at the C-terminus or the N-terminus of the antigen, preferred at the C-terminus.

As used herein, the term "S-Tag" and "S-protein" refers to oligopeptides derived from pancreatic ribonuclease A (RNase A).

In an embodiment the S-Tag of the protein-S-Tag fusion protein and the S-protein of the S-protein-tail piece (tp) fusion protein are wild type from pancreatic RNase A.

In a further embodiment the S-Tag of the protein-S-Tag fusion protein is selected from human (SEQ ID NO. 2), bovine (SEQ ID NO. 3), sheep (SEQ ID NO. 4), goat (SEQ ID NO. 5), pig (SEQ ID NO. 6), horse (SEQ ID NO. 7) or roe deer pancreatic RNase A (SEQ ID NO. 8) or an oligopeptide with a sequence identity of at least 70% to one of the sequences SEQ ID NO. 2 to 8, preferred a sequence identity of at least 85% to one of the sequences SEQ ID NO. 2 to 8 and mostly preferred a sequence identity of at least 95% to one of the sequences SEQ ID NO. 2 to 8. The S-Tag is selected according to the use of the oligomeric protein according to the invention, for example the S-Tag from human pancreatic RNase A (SEQ ID No. 2) for the use in vaccines for humans.

In an embodiment the S-Tag of the protein-S-Tag fusion protein comprises one of the sequences SEQ ID NO. 2 to 8.

In an embodiment the S-Tag of the protein-S-Tag fusion protein comprises one of the sequences SEQ ID NO. 2 to 8, wherein the S-Tag is 15 to 20 amino acids long, preferred 15 amino acids.

In a further embodiment the S-Tag of the protein-S-Tag fusion protein is an 11 to 19 amino acids long, preferred 13 to 17 amino acids long and mostly preferred a 15 amino acid long, oligopeptide with a sequence identity of at least 70% to one of the sequences SEQ ID NO. 2 to 8, preferred a sequence identity of at least 85% to one of the sequences SEQ ID NO. 2 to 8 and mostly preferred a sequence identity of at least 95% to one of the sequences SEQ ID NO. 2 to 8.

In an embodiment the S-protein of the S-protein-tail piece (tp) fusion protein is selected from human (SEQ ID NO. 9), bovine (SEQ ID NO. 10), sheep (SEQ ID NO. 11), goat (SEQ ID NO. 12), pig (SEQ ID NO. 13), horse (SEQ ID NO. 14) or roe deer pancreatic RNase A (SEQ ID NO. 15). The S-protein is selected according to the use of the oligomeric protein according to the invention, for example the S-protein from human pancreatic RNase A (SEQ ID NO. 9) for the use in vaccines for humans.

In an embodiment the S-protein of the S-protein-tail piece (tp) fusion protein comprises one of the sequences SEQ ID NO. 9 to 15.

In an embodiment the S-protein of the S-protein-tail piece (tp) fusion protein comprises one of the sequences SEQ ID NO. 9 to 15, wherein the S-protein is 109 to 150 amino acids long, preferred 109 to 120 amino acids.

In an embodiment the S-protein of the S-protein-tail piece (tp) fusion protein comprises a 80 to 140 amino acids long, preferred 100 to 120 amino acids long and mostly preferred a 109 to 113 amino acid long, oligopeptide with a sequence identity of at least 65% to one of the sequences SEQ ID NO. 9 to 15, preferred a sequence identity of at least 80% to one of the sequences SEQ ID NO. 9 to 15 and mostly preferred a sequence identity of at least 95% to one of the sequences SEQ ID NO. 9 to 15.

As used herein, the term "tail piece (tp)" refers to an oligopeptide derived from a heavy chain of an IgM or IgA antibody. Advantageously, the tp forms disulfides with other tp molecules and thus the protein-S-Tag fusion protein bond to the S-protein-tp fusion protein is able to oligomerise.

In a further embodiment the tp of the S-protein-tp fusion protein is selected from human (SEQ ID NO. 16), mouse (SEQ ID NO. 17), gorilla (SEQ ID NO. 18), monkey (SEQ ID NO. 19), dog (SEQ ID NO. 20), giant panda (SEQ ID NO. 21), rabbit (SEQ ID NO. 22), Asian house shrew (SEQ ID No. 30), cattle (SEQ ID No. 31), turtle (SEQ ID No. 32), hamster (SEQ ID No. 33), or an alternative human variant (SEQ ID No. 34) as well as sequences with a sequence identity of at least 75%, preferably 85%, more preferably 90%, mostly preferred 95%, sequence identity to one of the sequences SEQ ID NO. 16 to 22 or 30 to 34. The tp is selected according to the use of the oligomeric protein according to the invention, for example the human tp (SEQ ID No. 16 or SEQ ID No. 34) for the use in vaccines for humans.

In an embodiment the tp of the S-protein-tp fusion protein comprises one of the sequences SEQ ID NO. 16 to 22 or SEQ ID NO. 30 to 34.

In an embodiment the tp of the S-protein-tp fusion protein comprises one of the sequences SEQ ID NO. 16 to 22 or SEQ ID NO. 30 to 34, wherein the tp is 19 to 25 amino acids long, preferred 19 amino acids.

In an embodiment the tp of the S-protein-tp fusion protein comprises a 15 to 25 amino acids long, preferred 17 to 21 amino acids long and mostly preferred 19 amino acids long, oligopeptide with a sequence identity of at least 75% to one of the sequences SEQ ID NO. 16 to 22 or SEQ ID NO. 30 to 34, preferred a sequence identity of at least 85% to one of the sequences SEQ ID NO. 16 to 22 or SEQ ID NO. 30 to 34 and mostly preferred a sequence identity of at least 95% to one of the sequences SEQ ID NO. 16 to 22 or SEQ ID NO. 30 to 34, wherein the position of the cysteine (Cys, C) residue is constant.

In a further embodiment the co-expression according to step a) comprises the step of provision of genes encoding the two fusion proteins in an expression cassette and transfer of the expression cassette into a shuttle vector.

In an embodiment the shuttle vector is selected from agrobacteria harbouring shuttle vectors, preferred a pCB301 vector.

In a further embodiment the expression cassette comprises a promoter selected from USP promoter, Legumin promoter, β-phaseolin promoter, CaMV35S promoter or Patatin promoter. In an embodiment the expression in seeds is carried out with USP promoter, Legumin promoter or β-phaseolin promoter, the expression in leaves with CaMV35S promoter, and the expression in tubers with Patatin promoter or CaMV35S promoter.

In a further embodiment the step of provision of genes encoding the two fusion proteins further comprises a shuttle vector for expression of HcPro. Advantageously, HcPro is a suppressor of gene silencing that has been found to enhance remarkably the expression levels of recombinant proteins in plant cells (Conley et al. 2009, Sudarshana et al. 2006).

In a further embodiment the co-expression according to step a) comprises the step of provision of genes encoding the two fusion proteins in plant cells by co-infiltration of plant cells with agrobacterium strains comprising genes encoding the two fusion proteins (Agro-infiltration).

As used herein, the term "Agro-infiltration" refers to the infiltration of plant cells with agrobacterium strains.

In a further embodiment the provision of genes encoding the two fusion proteins in plant cells by Agro-infiltration is carried out with *Agrobacterium tumefaciens*.

In a further embodiment the provision of genes encoding the two fusion proteins in plant cells by Agro-infiltration is carried out under vacuum. As used herein, the term "vacuum" refers to a gaseous pressure less than atmospheric pressure.

In a further embodiment the co-expression according to step a) is carried out in endoplasmic reticulum (ER) of eukaryotic cells.

According to the invention the co-expression according to step a) is followed by the extraction of the two fusion proteins.

In a further embodiment the extraction of the two fusion proteins is carried out with an aqueous buffer solution with a pH value of 6 to 9 preferred a phosphate buffered saline with a pH value of 7.4 and 0.88% sodium chloride.

In a further embodiment the method for production of an oligomeric protein in eukaryotic cells further comprises after step a) and b) the steps c) Precipitation with salt, preferred sodium chloride, and/or heat, d) Filtration and e) Solvation in an aqueous solution.

In a further embodiment the method for production of an oligomeric protein in eukaryotic cells further comprises the step of analysis of the eukaryotic cells after step a) and/or step b).

In a further embodiment the analysis of the eukaryotic cells after step a) and/or step b) comprises the analysis of genomic DNA, protein analysis and/or physiological analysis.

The biologic activity of the oligomeric protein, wherein the protein is an antigen, can be demonstrated by indirect enzyme linked immunosorbent assay (ELISA). The biologic activity of the oligomeric protein, wherein the protein is an antigen binding unit, can be demonstrated by enzyme linked immunosorbent assay (ELISA).

In a further embodiment the method for the production of an oligomeric protein in eukaryotic cells further comprises after step a) and b) the addition of an adjuvant. Advantageously, adjuvants enhance the antigenicity by a depot effect, enhancing the ability to pass membranes and/or enhancing the activity of immunocompetent cells, e.g. T cells, B cells or macrophages. In a further embodiment the adjuvant is selected according to the oligomeric antigen. In an embodiment the adjuvant is selected from oil-in-water emulsified adjuvants, preferred Emulsigen®-D adjuvant (MVP Technologies, NE, US).

The present invention further comprises an oligomeric protein comprising at least a first fusion protein comprising a protein and an S-Tag (in the following also called protein-S-Tag fusion protein),
wherein the protein is an antigen or an antigen binding unit, and
a second fusion protein comprising a S-protein and a tail piece (tp) (in the following also called S-protein-tail piece (tp) fusion protein),
wherein the tail piece (tp) is an oligopeptide derived from a heavy chain of an IgM or IgA antibody.

Advantageously, the tp constitutes the oligomerisation of the protein, viz. of the antigen or antibody.

Advantageously, the oligomeric protein comprising at least a protein-S-Tag fusion protein and a S-protein-tail piece (tp) fusion protein exhibits a high stability. As used herein, the term "high stability" refers to the stability of the extracted oligomeric proteins, preferred in an aqueous buffer solution with a pH value of 6 to 9, mostly preferred a phosphate buffered saline with a pH value of 7.4 and 0.88% sodium chloride; at temperatures of up to 8° C., preferred 0° C. to 4° C., for up to a few weeks, preferred a few months.

In a further embodiment the oligomeric protein comprises at least one adjuvant. Advantageously, adjuvants enhance the antigenicity by a depot effect, enhancing the ability to pass membranes and/or enhancing the activity of immunocompetent cells, e.g. T cells, B cells or macrophages. In a further embodiment the adjuvant is selected according to the oligomeric antigen. In an embodiment the adjuvant is selected from oil-in-water emulsified adjuvants, preferred Emulsigen®-D adjuvant (MVP Technologies, NE, US).

In a further embodiment the oligomeric protein is obtained by the method according to the invention.

Another object of the invention is a nucleic acid comprising a nucleic acid sequence encoding an oligomeric protein according to the invention or a vector comprising such a nucleic acid.

The term "nucleic acid" as used herein includes deoxyribonucleic acids (DNA) and ribonucleic acids (RNA). Nucleic acids in the form of DNA are preferred.

The term "vector" as used herein includes a plasmid, virus or other nucleic acid carriers, that comprise a nucleic acid sequence according to the invention by genetic recombination (recombinantly), e.g. by insertion or incorporation of said nucleic acid sequence. Prokaryotic vectors as well as eukaryotic vectors are applicable for the invention. Prokaryotic vectors are preferably used in the invention to transfect *agrobacterium* strains.

In an embodiment the nucleic acids comprise at least the nucleic acid sequences SEQ ID NO.28 and SEQ ID NO. 29.

In an embodiment the nucleic acid is the nucleic acid sequence encoding an oligomeric protein according to the invention.

The invention further encompasses the use of a nucleic acid comprising a nucleic acid sequence encoding an oligomeric protein according to the invention or a vector comprising such a nucleic acid in the production of an oligomeric protein according to the invention.

The present invention further comprises a cell or non-human host organism comprising a nucleic acid or a vector according to the invention.

Preferably the cell or non-human host organism is used for the production of the oligomeric protein according to the invention.

A cell or non-human host organism within the sense of the invention is a naturally occurring cell or a (optionally transformed or genetically modified) cell line or organism that comprises at least one vector according to the invention or a nucleic acid according to the invention artificially, as described above. Thereby, the invention includes transient transfectants (e.g. by mRNA injection) or cells that include at least one vector according to the invention. Embryonal stem cells derived by killing of human embryos are preferably specifically excluded from the term "cells" within the sense of the invention.

The cell is preferably selected from cells of eukaryotes. Preferred eukaryotic cells are selected from plant cells. The non-human host organism is preferably a plant.

The present invention further comprises the use of the oligomeric protein according to the invention in vaccines. As used herein, the term "vaccine" refers to protein preparation that provides immunity to a particular disease. Vaccines can be prophylactic or therapeutic.

In a further embodiment the oligomeric protein according to the invention is used in active and passive vaccines.

In a further embodiment the oligomeric protein according to the invention is used in influenza vaccines.

In a further embodiment the oligomeric protein according to the invention is used in edible vaccines, preferred edible passive vaccines against a pathogen of the gastrointestinal tract, mostly preferred the oral cavity or the intestines; or the respiratory system. As used herein, the term "edible vaccines" refers to vaccines which are orally administered, for example feeding transgenic seeds containing vaccines.

Advantageously, the production of antibodies for passive immunization in seeds for the production of edible passive vaccines is accompanied by minimal downstream processing cost.

Advantageously, the oligomeric protein according to the invention is highly stable, wherein the stability in the intestinal tract is crucial for the successful development of edible vaccines.

In a further embodiment the oligomeric protein according to the invention or obtained by a method according to the invention is used for the manufacture of a vaccine.

The present invention further comprises a vaccine comprising the oligomeric protein according to the invention.

Advantageously, the oligomerisation of the protein, viz. of the antigen or antibody, enhances the immune response and the vaccine efficacy.

In a further embodiment the vaccine further comprises at least one adjuvant. In a further embodiment the adjuvant is selected from oil-in-water emulsified adjuvants, preferred Emulsigen®-D adjuvant (MVP Technologies, NE, US).

Advantageously, oil-in-water emulsified adjuvants form a mobile depot of the oligomeric protein according to the invention which can target immune effector cells and enhance the immune response and vaccine efficacy.

In a further embodiment the recently described embodiments can be combined.

FIGURES AND EXAMPLES

The present invention will now be further explained by the following non limiting figures and examples.

FIG. 1 shows a model of oligomer formation by co-expression of H5-S-Tag and multimeric S-protein-tp. The oligomeric state of the S-protein-tp is dependent on oligomeric state of the wild type S-protein which is a mixture of the dominant monomer as well as minor dimer, trimer etc. Fusion of wild type S-protein to tp causes additional linkage via disulfide bonds to generate multiple S-proteins. S-protein-tp depicted here as an example is a homodimer formed by a disulfide bond.

FIG. 2 shows the results of an anti-cmyc-Tag Western blot of hemagglutinin derivatives and S-protein derivatives in plant extracts compared with the S-protein-tp without His-tag in the oligomer purified by IMAC.

FIG. 3 shows expression cassettes for the in planta production of H5-S-Tag,H5Dk-S-Tag variant and eGFP-S-Tag, as well as S-Protein fusion proteins. CaMV35S Pro: Cauliflower mosaic virus 35S ubiquitous promoter; CaMV35S Term: Cauliflower mosaic virus 35S terminator.

FIG. 4 shows the hemagglutination titers of plant extracts and inactivated virus rg A/swan/Germany/R65/2006 (H5N1). WT: wild type *N. benthamiana*, PBS: phosphate buffered saline.

FIG. 5 shows the hemagglutination titer of size exclusion chromatography fractions of H5 oligomers and H5-S-Tag and the Western blot analysis of H5 oligomer and H5-S-Tag fractions. Protein purification by immobilized metal affinity chromatography (IMAC)-purified H5 oligomers or H5-S-Tag (each 63 µg in 0.5 ml) were separated on Suprose™6 increase 10/300 GI and fractions were analyzed by hemagglutination assay.

FIG. 6 shows the immunological characterization of H5 oligomer, H5-S-Tag and S-protein-tp extracts compared to wild type extracts: A) Measurement of antibody responses after two immunizations against purified hemagglutinin by indirect ELISA and raised by injection of different extracts into mice. P=P-value. B) Measurement of hemagglutination inhibition titers of sera raised against the mentioned extracts.

FIG. 7 shows the immunological characterization of H5 oligomer, H5-S-Tag and S-protein-tp extracts compared to wild type extracts: A) Measurement of antibody responses after three immunizations against purified hemagglutinin by indirect ELISA and raised by injection of different extracts into mice. P=P-value. B) Measurement of hemagglutination inhibition titers of sera raised against the mentioned extracts.

Figure 10:
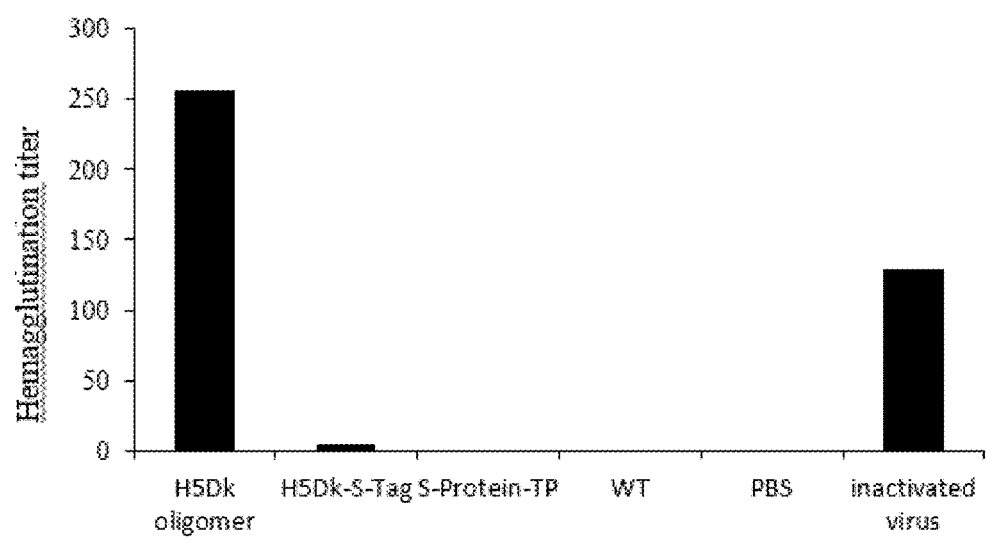

FIG. 10 shows the hemagglutination titers of plant extracts and inactivated virus rgA/swan/Germany/R65/2006 (H5N1). WT: wild type *N. benthamiana*, PBS: phosphate buffered Saline.

Construction of Plant Expression Vectors

The DNA sequences corresponding to aa 2-564 hemagglutinin of A/duck/Viet Nam/TG24-01/2005 (H5N1) strain and aa 21-124 S-Protein (UniProtKB accession numbers: Q14RX0 and P61823, respectively) were synthesized commercially (GENECUST EUROPE, Luxembourg) and provided in pUC57 vectors designated as pUC57-H5TG and pUC57-S-Protein.

Figure 1:
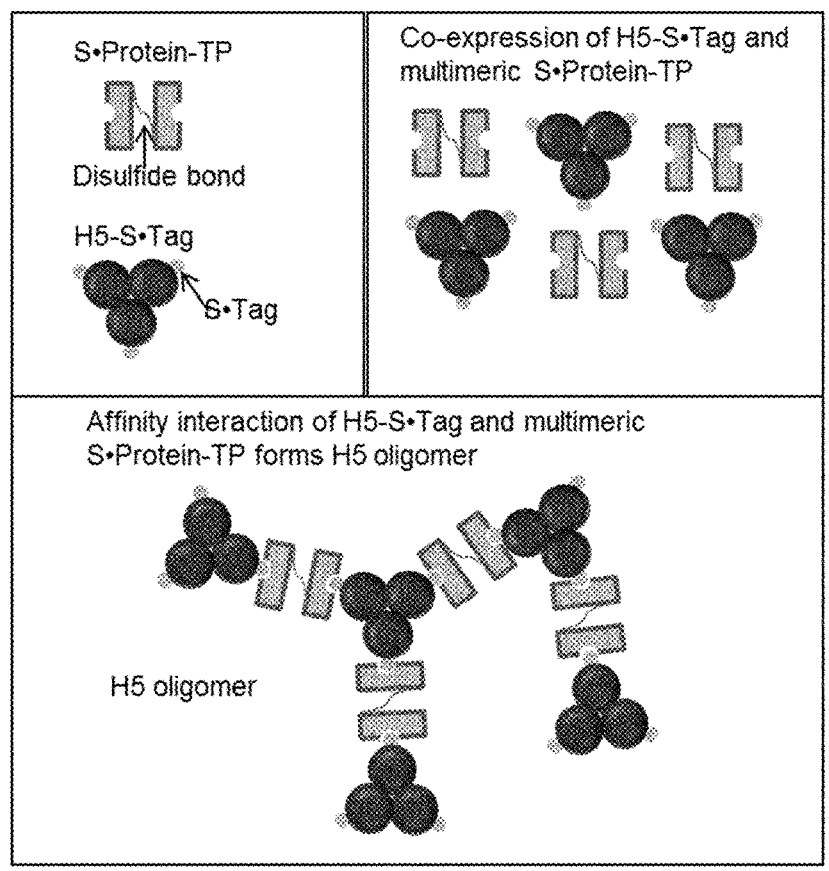
Figure 2:
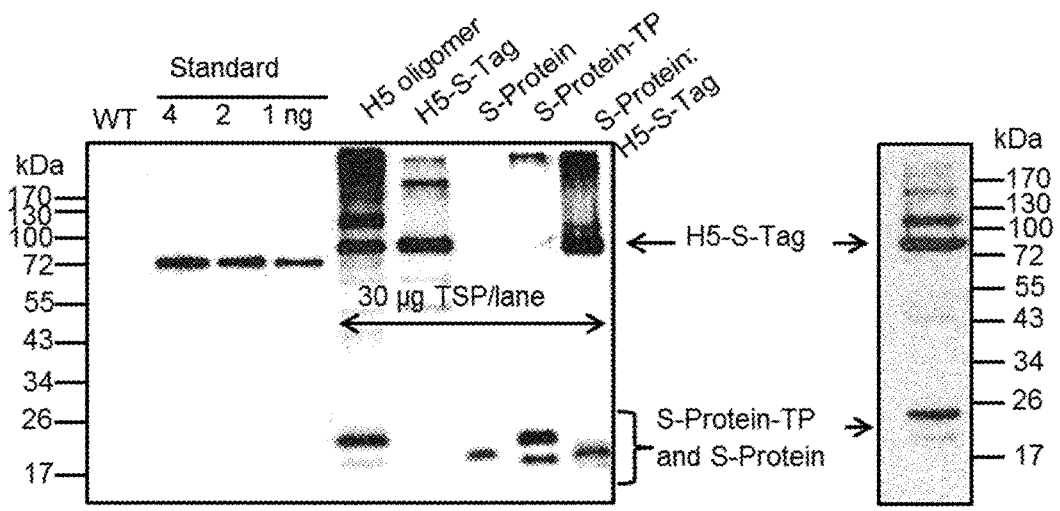

To express a wild type S-Protein, the DNA sequence coding for S-Protein was cloned into the pRTRA-35S-H5pII at BamHI and NotI to form a recombinant vector designated as the pRTRA-S-Protein (Phan et al. 2013). To multimerize S-Protein, DNA sequences coding for S-Protein were introduced into pRTRA vectors which contain trimerized (GCN4-pII) (reference 1) or dimerized (GCN4 wild type) domains (reference 2) (Harbury et al. 1993), and a tail piece of mouse IgM antibody responding for disulfide bond formation via its cysteine residues to create pRTRA-His-S-Protein-GCN4pII (reference 1) and pRTRA-His-S-Protein-GCN4 wt (reference 2), pRTRA-S-Protein-tp, for expression of S-Protein-pII (reference 1) (SEQ ID NO. 23), S-Protein- GCN4 (reference 2) (SEQ ID NO. 24), S-Protein-tp (SEQ ID NO. 25), respectively (FIG. 2 and Tab. 1). A S-Tag coding sequence flanked by NotI and NheI sites was designed and inserted via the mentioned restriction sites into pRTRA-H5TG-GCNpII to produce pRTRA-H5TG-GCNpII-S-Tag vector that was used for expression of trimerized H5-S-Tag (SEQ ID NO. 26).

FIG. 2 shows the results of an anti-cmyc-Tag Western blot of hemagglutinin derivatives and S-protein derivatives in plant extracts compared with the S-protein-tp without His-tag in the oligomer purified by IMAC: Standard: anti-TNFα-nanobody ELP, S-Protein-H5-S-Tag co-expression, H5 oligomer: S-Protein-tp-H5-S-Tag co-expression. Expression of the different components at the expected sizes could be shown by Western-Blot. The potentially neutralizing antibody response was significantly better after immunization with H5 oligomer extracts compared to the sera of mice immunized with H5-S-Tag trimer extracts ($P<0.001$).

Five expression cassettes in pRTRA vectors (pRTRA-S-Protein, pRTRA-His-S-Protein-GCN4 wt, pRTRA-S-Protein-tp, pRTRA-H5TG-GCNpII-S-Tag) constructed (FIG. 3) were cloned into the shuttle pCB310 vectors at Hind III restriction sites. The shuttle pCB310 vectors were introduced into the agrobacterial AGV2206 strain.

TABLE 1

Expression and functionality profiles of recombinant influenza hemagglutinin and S-Protein variants. A single protein or two proteins (one of the S-Protein variants and H5-S-Tag) were expressed or co-expressed transiently in plants, respectively, and measured by Western blot. The oligomer formation of all variants was investigated by hemagglutination assay.

| Proteins | Protein expression | hemagglutination unit (HAU) |
|---|---|---|
| S-Protein | (+) | 0 |
| S-Protein-tp | (+) | 0 |
| S-Protein-pll (reference 1) | (+) | 0 |
| S-Protein-GCN4 (reference 2) | (+) | 0 |
| H5-S-Tag | (+) | 0 |

| Proteins | Protein expression | hemagglutination unit (HAU) Co-expression with H5-S-Tag in plants in vivo | hemagglutination unit (HAU) Combination with H5-S-Tag in vitro |
|---|---|---|---|
| S-Protein | (++) | 4 | 0 |
| S-Protein-tp | (++) | 256 | 0 |
| S-Protein-pll (reference 1) | (++) | 0 | 0 |
| S-Protein-GCN4 (reference 2) | (++) | 2 | 0 |

(+) and (++): Expression of a single protein or both proteins confirmed by Western blot.

Agro-Infiltration

Agro-infiltration for expression of recombinant proteins was described in detail by Phan and Conrad (Phan and Conrad 2016) and is briefly described here. *Agrobacteria* harbouring shuttle vectors for expression of recombinant proteins (see FIG. 2) and the plant vector for expression of HcPro which is a suppressor of gene silencing that has been found to enhance remarkably the expression levels of recombinant proteins in plant cells (Conley et al. 2009, Sudarshana et al. 2006) were pre-cultivated separately in lysogeny broth (LB) medium with 50 μg/ml kanamycin, 50 μg/ml carbenicillin and 50 μg/ml rifampicin overnight at 28° C. and 140 rpm. The precultures were added to 40 ml of a new LB culture. After further 24 h of cultivation, bacteria were harvested by centrifugation at 4000 g, 10 min, 4° C. and resuspended in infiltration buffer (10 mM 2-(N-morpholino) ethanesulphonic acid (MES), 10 mM $MgSO_4$, pH 5.6). *Agrobacteria* harbouring the shuttle vector for expression of recombinant protein and the plant vector for expression of HcPro were combined and were diluted in infiltration buffer to a final optical density (OD) measured at a wavelength of 600 nm of 1.0. *N. benthamiana* plants (six to eight weeks old) were infiltrated by completely submerging each plant in the *Agrobacterium*-containing cup standing inside of a desiccator. Vacuum was applied for 2 min and then quickly released. The plants were then placed in the greenhouse at 21° C., 16 h light per day. Five days after infiltration, leaf samples were harvested and stored at −80° C.

Protein Purification by Immobilized Metal Affinity Chromatography (IMAC)

Five days after vacuum agrobacterial infiltration, leaf sample was harvested, frozen in liquid nitrogen and homogenized using a commercial blender. Total proteins were extracted in 50 mM Tris buffer (pH 8.0). The extracts were clarified by centrifugation (18,000 g, 30 min, 4° C.) and then filtrated through paper filters. The clarified extracts were mixed with Nickel-nitrilotriacetic acid (Ni-NTA) resin agarose washed twice with water before. After mixing for 30 min at 4° C., the mixture was applied to a chromatography column. Thereafter, the column was extensively washed (50 mM $NaH_2PO_4$, 300 mM NaCl, 30 mM Imidazole, pH 8.0). Recombinant proteins were then eluted from the column by elution buffer (50 mM $NaH_2PO_4$, 300 mM NaCl, 125 mM Imidazole, pH 8.0), filled into dialysis bags, concentrated with poly(ethylene glycol) (PEG) 6000 and dialyzed against PBS.

Purification of H5 Oligomer by Using *Galanthus nivalis* (GLN)-Linked Agarose

Frozen leaf samples (40 g) were homogenized in liquid nitrogen. Total protein was extracted in PBS buffer (137 mM NaCl, 2.7 mM KCl, 10 mM $Na_2HPO_4$, 1.8 mM $KH_2PO_4$, pH 7.5). The extract was centrifuged twice (23,000 rpm, 30 min, 4° C.) and mixed with 10 ml of GLN resin previously washed twice with water and once with PBS buffer. After mixing at 4° C. for 30 min, the mixture was applied to a chromatography column. Thereafter, the column was washed twice with 30 ml PBS buffer. Recombinant protein was then eluted from the column with 10 ml elution buffer (137 mM NaCl, 2.7 mM KCl, 10 mM $Na_2HPO_4$, 1.8 mM $KH_2PO_4$, 200 mM α-methylmannoside, pH 7.4). The protein solution was dialyzed against PBS at 4° C. overnight and concentrated by using poly(ethylene glycol) (PEG) 6000.

Size Exclusion Chromatography (SEC)

34 μg protein in 0.5 ml of purified H5 oligomers and H5-S-Tag, respectively, were loaded onto a Superose™ 6 Increase 10/300 GL column (GE Healthcare). The high molecular weight kit contains standard proteins with molecular weights in the range of 44 kDa to 2000 kDa which were loaded onto the column to estimate the molecular weight of proteins of interest. 500 μl per fraction was collected for hemagglutination test and Western blot analysis.

For ELISA test, affinity-purified trimeric hemagglutinin as an antigen was further purified via the column with starting concentrations of 1.25 mg protein in 0.5 ml.

SDS-PAGE and Western Blotting

Extracted plant proteins, 10 ng of the IMAC and SEC purified hemagglutinin or an anti-TNFα-nanobody-ELP standard protein (Conrad et al. 2011) were separated by reducing SDS-PAGE (10% polyacrylamide) and then electrotransferred to nitrocellulose membranes. The Wester blotting procedure was carried out according to Phan et Conrad (Phan et Conrad 2016). The Western blotting procedure was carried out using monoclonal anti-c-myc antibodies followed the protocol described by Gahrtz et Conrad (Gahrtz et Conrad 2009). Sheep anti-Mouse IgG, Horseradish Peroxidase linked whole antibody was used as the secondary antibody (Secondary antibodies, GE healthcare UK limited Little Chalfont BuckinghamShire HP7 9NA UK) followed by Enhanced Chemiluminescence-based detection (ECL). To detect H5-specific mouse antibodies, ten mouse sera from each group were mixed and membranes were incubated with the respective mixtures.

Mouse Immunizations

Hemagglutinin contents (H5 oligomer and H5-S-Tag) in plant extracts were semi-quantified by Western blotting. Plant extracts containing 100 ng of either H5 oligomers or H5-S-Tag were selected for mouse immunization. In control groups, the plant extract containing S-Protein-tp and the non-transformed plant extract which had the same amount of total soluble protein with plant extracts containing H5 oligomers and H5-S-Tag were used. All plant extracts were formulated with the Emulsigen®-D adjuvant (MVP Technologies, US) at 20% final concentration. Seven to nine weeks old male C57/Black6J mice (Charles River Laboratories, Research Models and Services, Germany GmbH; twelve per group) were subcutaneously immunized with Emulsigen®-D adjuvant-formulated plant extracts at days 0, 14 and 28. One week after the 2nd and 3rd immunization, mice were bled via the retro-orbital sinus. Mouse sera were collected individually for hemagglutination inhibition (HI) and ELISA tests.

Hemagglutination Test and Hemagglutination Inhibition Assay

The hemagglutination test was based on a standard protocol (World Organization for Animal Health (OIE) (2004) and described in detail in Phan et Conrad (Phan et Conrad 2016). The dilution that induced complete hemagglutination was defined as one hemagglutination unit (HAU). The hemagglutination inhibition (HI) assay was done similarly based on a standard procedure (World Organization for Animal Health (OIE) (2004). A 25 µl aliquot of a single mouse serum was placed in the first well of a microtitre plate containing 25 µl PBS, and twofold serial dilutions were done across the row of 8 wells. A 25 µl volume containing 4 HAU of the inactivated rg A/swan/Germany/R65/2006(H5N1) virus was added to the reaction and held at 25° C. for 30 min. Then 25 µl of 1% chicken red blood cells was added, and the plates were incubated at 25° C. for 30 min. The HI titer was presented as the reciprocal of the highest dilution of serum, which could completely inhibit hemagglutination.

Figure 4:
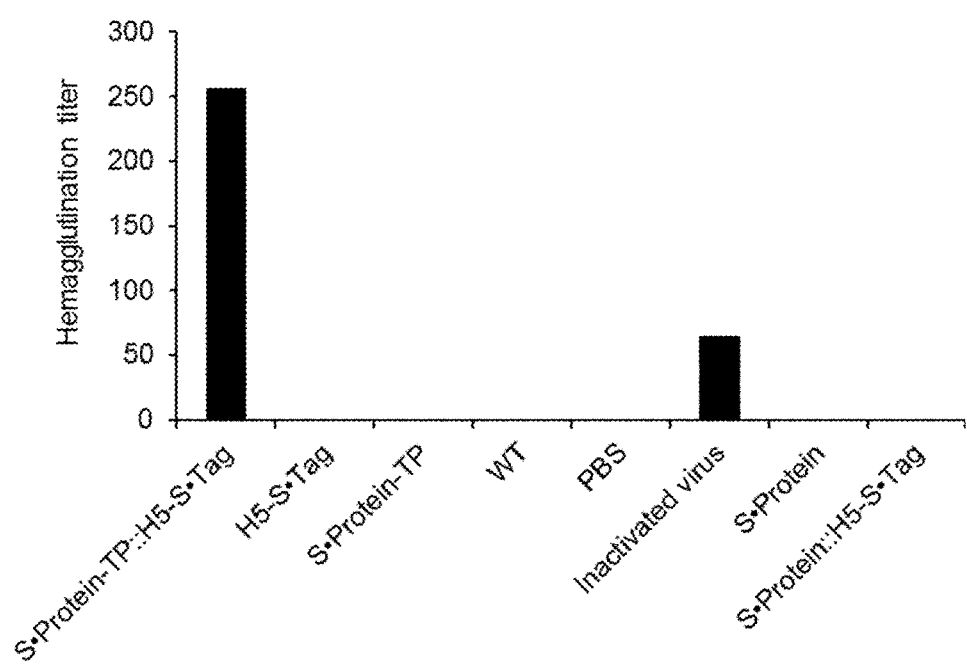

FIG. 4 and Tab. 1 show the hemagglutination titers of plant extracts and inactivated virus rg A/swan/Germany/R65/2006(H5N1). The hemagglutination titer caused by the co-expressed proteins was very low, whereas the both proteins were accumulated in the ER, indicating an insufficiently multimerization of the wild type S-protein.

Figure 5:
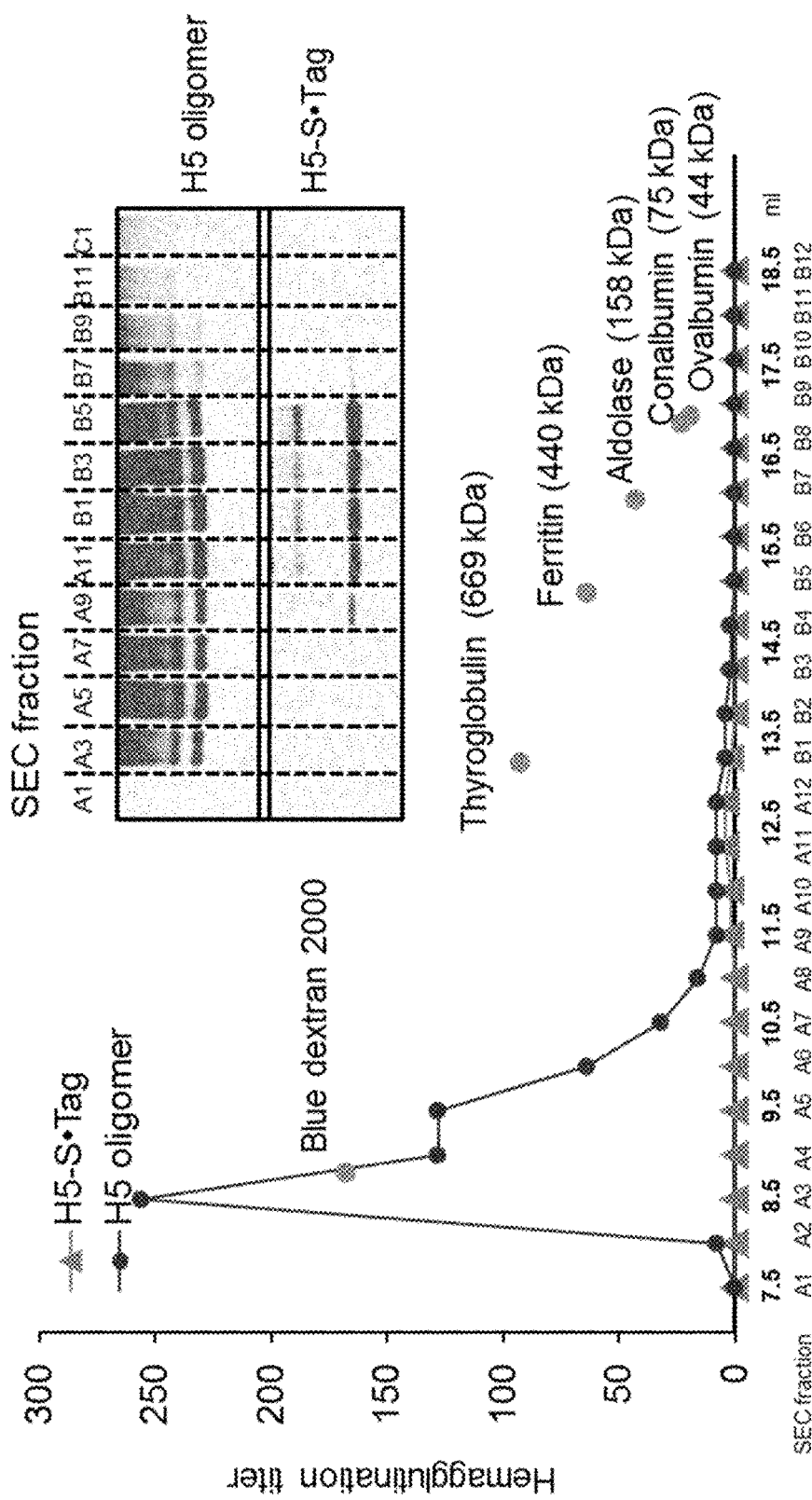

FIG. 5 shows the hemagglutination titer of size exclusion chromatography fractions of H5 oligomers and H5-S-Tag and the Western blot analysis of H5 oligomer and H5-S-Tag fractions. H5-S-Tag and H5 oligomer were purified by IMAC. The purified product was analyzed by Western blot. Both H5-S-Tag and S-protein-tp (without His-Tag) were detected indicating that S-protein-tp specifically interacted with the S-Tag. Purified H5 oligomer and H5-S-Tag were further separated by SEC and the hemagglutination titer of every fraction was estimated. High hemagglutination titers were observed in fractions A3 to A8 of H5 oligomers. The highest molecular weight (fraction A3, about 2,000 kDa) corresponds to the highest hemagglutination titer. The analysis of H5-S-Tag by SEC did not show a high molecular weight and no high hemagglutination titer. The fractions of H5-S-Tag and H5 oligomer were separated by SDS-PAGE and analyzed by Western Blot in parallel. High molecular weight hemagglutinins (700 kDa to 2,000 kDa, fractions A3 to A7) were exclusively achieved in H5 oligomer extracts after co-expression of H5-S-Tag and S-protein-tp.

Indirect Enzyme Linked Immunosorbant Assay (ELISA)

Microtiter plates (ImmunoPlate Maxisorp, Nalgen Nunc International, Roskilde, Denmark) were coated with 100 µl of 0.5 µg/mL of immobilized metal affinity chromatography (IMAC) and size exclusion chromatography (SEC) purified hemagglutinin (H5) trimer in phage PBS (100 mM NaCl, 32 mM $Na_2HPO_4$, 17 mM $Na_2HPO_4$, pH 7.2) and incubated overnight at room temperature. After blocking with 3% (w/v) bovine serum albumin (BSA), 0.05% (v/v) Tween20 in PBS (PBST) for 2 h, 100 µl of the specific dilution ($6 \cdot 10^{-4}$) were applied and incubated at room temperature for 1.0 h. Plates were washed 5 times with PBST, incubated with rabbit anti-mouse IgG alkaline phosphatase conjugate diluted (2000 times) in 1% (w/v) BSA and washed again. The enzymatic substrate, p-nitrophenyl phosphate (pNPP) in 0.1 M diethanolamine-HCl (pH 9.8), was added and the absorbance signal was measured at 405 nm after a 1 h incubation at 37° C.

Figure 6:
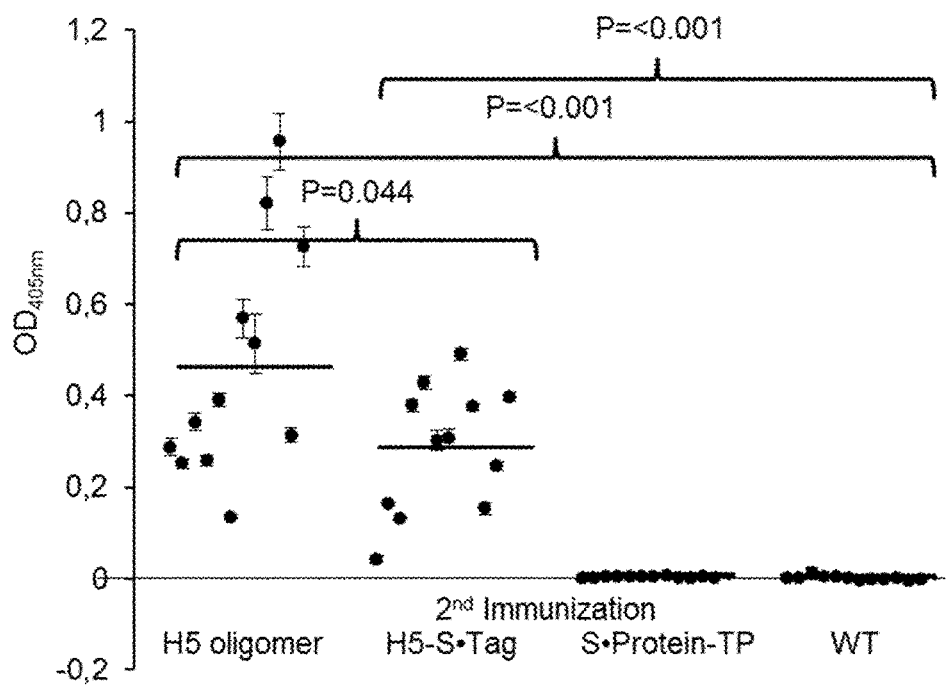
Figure 6:
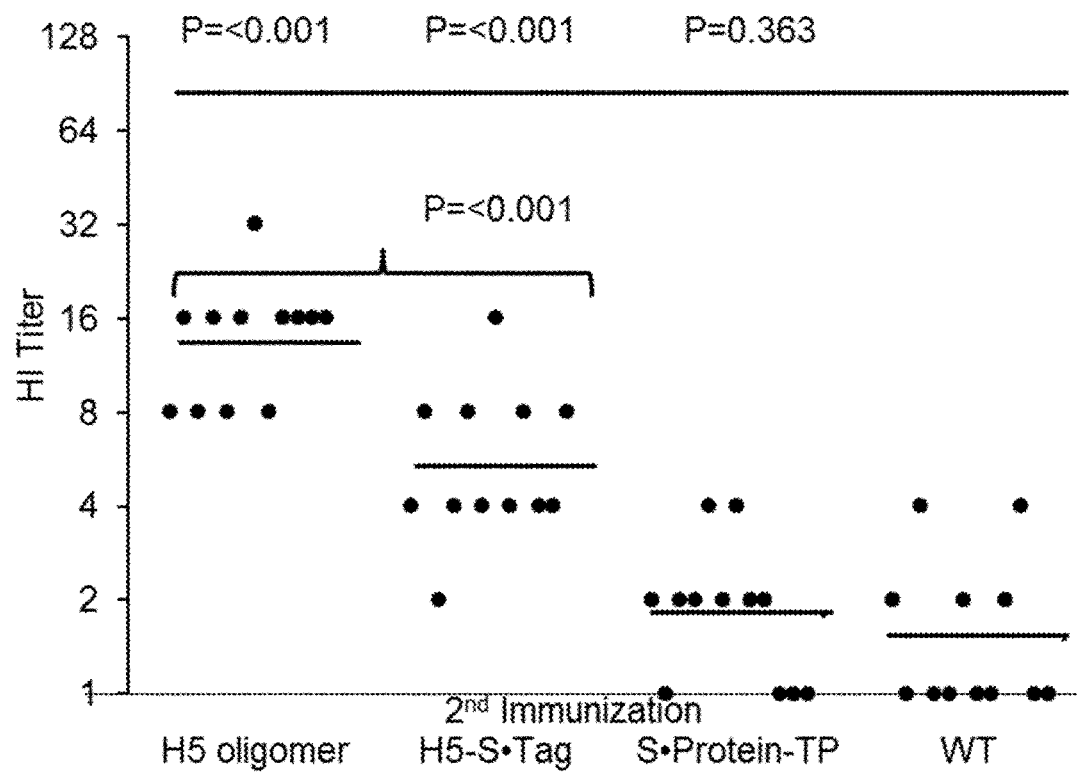
Figure 7:
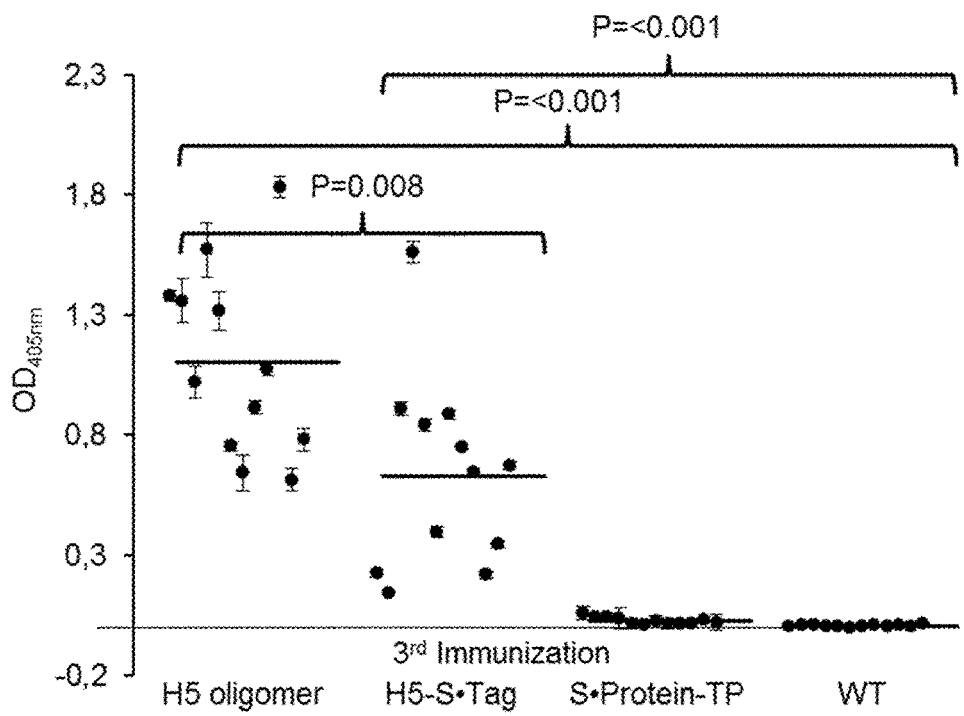
Figure 7:
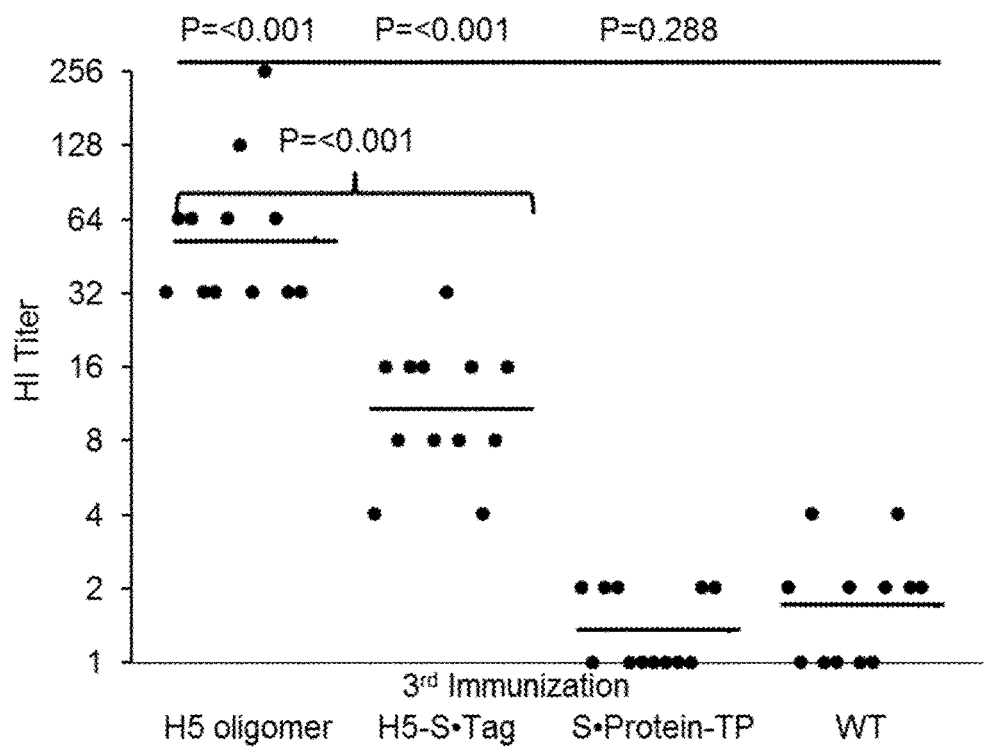

FIG. 6 A and FIG. 7 A show the measurement of antibody responses after two or three, respectively, immunizations against purified hemagglutinin by indirect ELISA and raised by injection of different extracts into mice. Specific immune responses tested against purified H5 were raised by immunization with H5 oligomer extracts and H5-S-Tag extracts as well. In controls, almost no immune responses against H5 were detected after immunization with S-protein-tp and with wildtype extracts. The humoral immune response tested against purified H5 was significantly better after immunization with H5 oligomer crude extracts (P=0.044 or 0.008, respectively). hemagglutination inhibition (HI) assays showed that potentially neutralizing antibodies inhibiting hemagglutination could be produced in mice by immunization with H5 oligomer extracts and with H5-S-Tag extracts (FIG. 6 B and FIG. 7 B).

Figure 8:
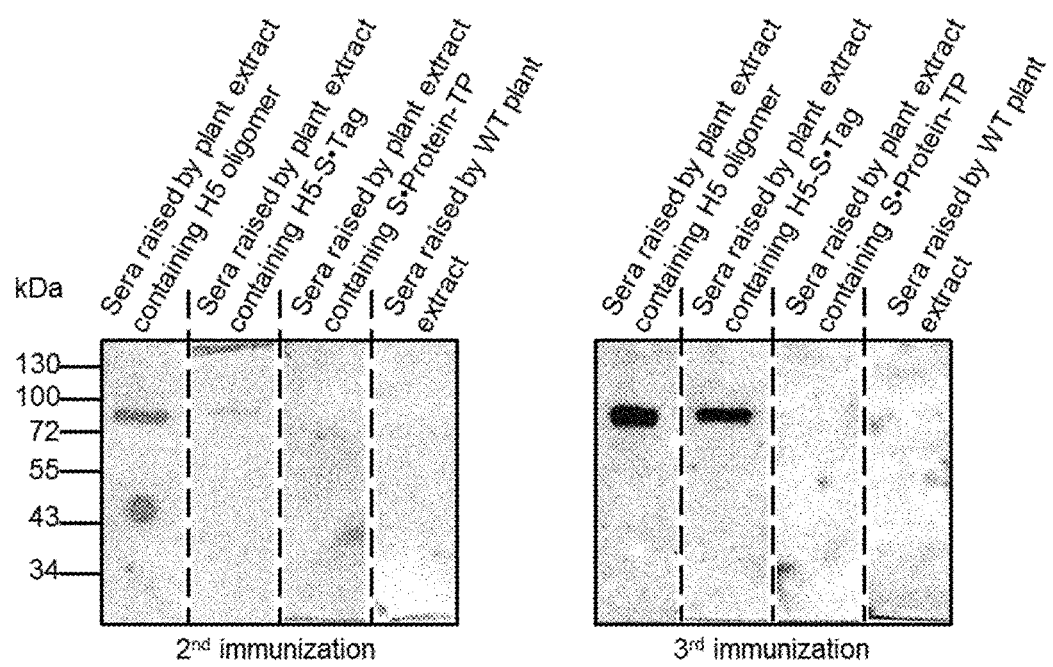
FIG. 8 shows the hemagglutin (H5) specific binding of antibodies from mixtures of 10 sera, respectively, raised against H5 containing extracts (extracts containing H5 oligomer, H5-S-Tag, S-protein-tp or WT plant extract) demonstrated by Western blot.
Figure 9:
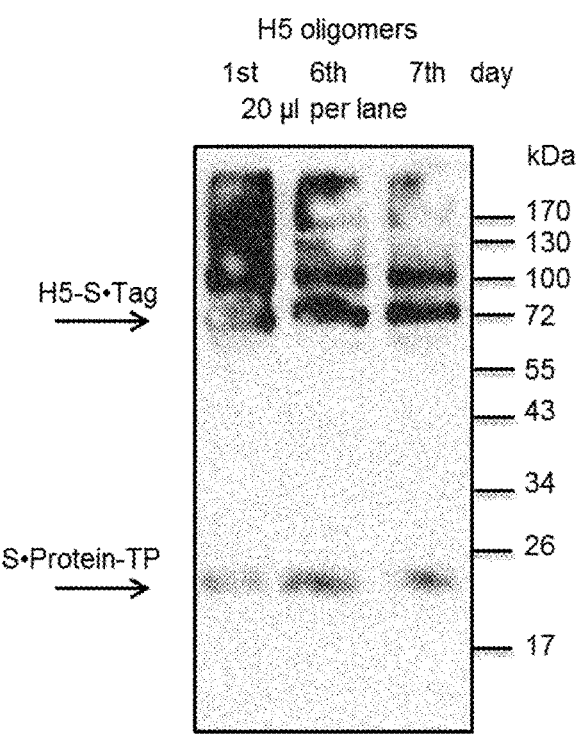
FIG. 9 shows the stability of immunogenic extracts revealed by A) Western Blot and B) hemagglutination titer.
Figure 9:
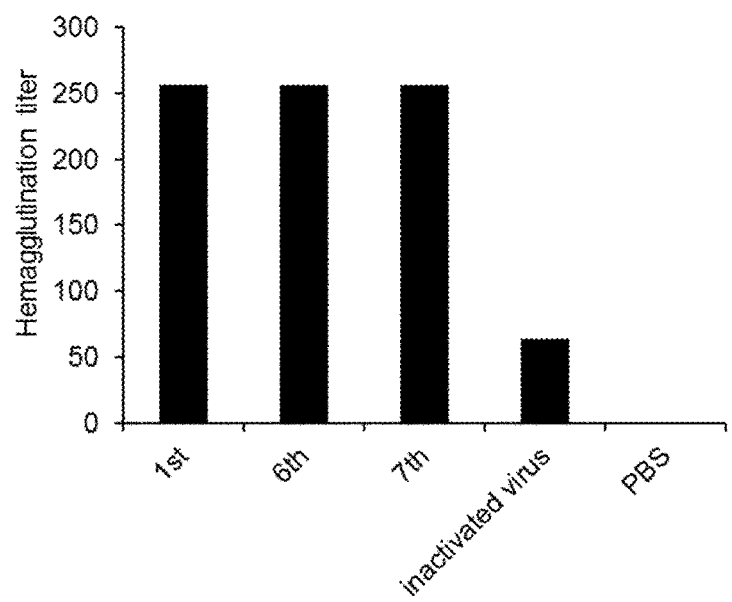

FIG. 8 shows the hemagglutinin (H5) specific binding of antibodies from mixtures of 10 sera, respectively, raised against H5 containing extracts (extracts containing H5 oligomer, H5-S-Tag, S-protein-tp or WT plant extract) demonstrated by Western blot. Sera of mice raised against H5 oligomer as well as sera raised against H5-S-Tag bound to purified hemagglutinin, but sera from mice immunized with H5 oligomer extracts showed a stronger reaction Stability Test The immunogenic extracts were stored at 4° C. for one week without loss of antigen content as revealed by Western Blot (FIG. 9 A) and hemagglutination titer (FIG. 9 B).

Statistical Analyses

Statistical analyses of the hemagglutination inhibition assay data and ELISA results were performed using Mann-Whitney Rank-Sum test from the Sigma Plot software. P values less than 0.05 were defined as significant difference.

Application to New Hemagglutinin from the New DkHT2-2014 Strain

Figure 3:
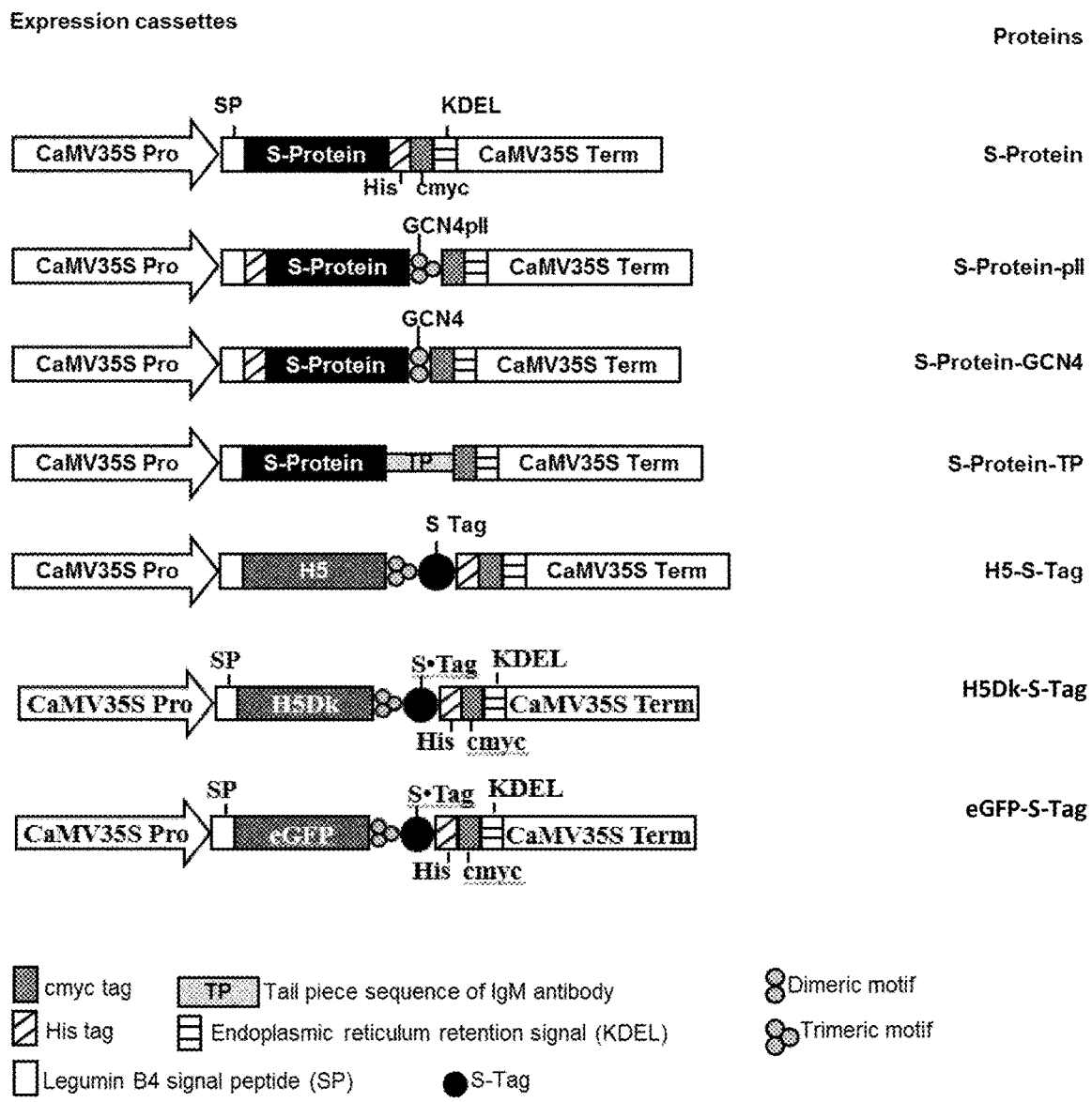

To verify our method used to produce oligomers by S-Tag and S-Protein interaction, the hemagglutinin from the new DkHT2-2014 strain (designated as H5Dk, SEQ ID No. 36)

currently circulating in Vietnam and enhanced Green Fluorescent Protein (eGFP, SEQ ID No. 37) are fused to S-Tag. The protein products are designated as H5Dk-S-Tag, eGFP-S-Tag, respectively. Expression cassettes for the in planta production presented in FIG. 3. The oligomers formed by co-expression of H5Dk-S-Tag and S-Protein-TP are designated as H5Dk oligomers and show very high hemagglutination titer in comparison with H5Dk (FIG. 10). Further analyses (size exclusion chromatography, mouse immunization . . . ) are currently running.

The deduced hemagglutinin amino acid sequence similarity of new hemagglutinin (H5Dk, SEQ ID No. 36) and A/duck/Viet Nam/TG24-01/2005(H5N1) strain (SEQ ID No. 35) is 93%.

CITED NON-PATENT LITERATURE

R. J. Cox, K. A. Brokstad, P. Ogra (2004) Influenza virus: immunity and vaccination strategies. Comparison of the immune response to inactivated and live, attenuated influenza vaccines. Scand. J. Immunol. 59, 1-15.

H. L. Yen, R. G. Webster (2009) In: R. W. Compans, W. A. Orenstein (Eds.): Vaccines for pandemic influenza, Vol. 333, 3-24.

E. Topp, R. Irwin, T. McAllister, M. Lessard, J. J. Joensuu, I. Kolotilin, U. Conrad, E. Stöger, T. Mor, H. Warzecha, J. C. Hall, M. D. McLean, E. Cox, B. Devriendt, A. Potter, A. Depicker, V. Virdi, L. Holbrook, K. Doshi, M. Dussault, R. Friendship, O. Yarosh, H. S. Yoo, J. MacDonald, R. Menassa (2016) The case for plant-made veterinary immunotherapeutics. Biotechnol. Adv. 34 597-604.

N. Landry, B. J. Ward, S. Trépanier, E. Montomoli, M. Dargis, G. Lapini, L.-P. Vézina (2010) Preclinical and Clinical Development of Plant-Made Virus-Like Particle Vaccine against Avian H5N1 Influenza. PLoS ONE 5, e15559.

M.-A. D'Aoust, P.-O. Lavoie, M. M.-J. Couture, S. Trepanier, J.-M. Guay, M. Dargis, S. Mongrand, N. Landry, B. J. Ward, L.-P. Vezina (2008) Influenza Virus-Like Particles Produced by Transient Expression in Nicotiana Benthamiana Induce a Protective Immune Response Against a Lethal Viral Challenge in Mice. Plant Biotechnol. J. 6 (9), 930-940.

H. T. Phan et al. (2013) ELPylated haemagglutinins produced in tobacco plants induce potentially neutralizing antibodies against H5N1 viruses in mice. Plant Biotechnol. J. 11, 582-593.

P. Harbury, T. Zhang, P. Kim, T. Alber (1993) A switch between two-, three-, and four-stranded coiled coils in GCN4 leucine zipper mutants. Science 262, 1401-1407.

D. M. Czajkowsky, J. Hu, Z. Shao, R. J. Pleass (2012) Fc-fusion proteins: new developments and future perspectives. EMBO Mol. Med. 4, 1015-1028.

S. Loureiro, J. Ren, P. Phapugrangkul, C. A. Colaco, C. R. Bailey, H. Shelton, E. Molesti, N. J. Temperton, W. S. Barclay, I. M. Jone (2011) Adjuvant-Free Immunization with Hemagglutinin-Fc Fusion Proteins as an Approach to Influenza Vaccines. Journal of Virology 85, 3010-3014.

T. Asai, L. A. Wims, S. L. Morrison (2005) An Interaction between S-tag ans S-protein derived from human ribonuclease 1 allows site-specific conjugation of an enzyme to an antibody for targeted drug delivery. J. Immunol. Methods 299, 63-76.

C.-J. Wei, L. Xu, W.-P. Kong, W. Shi, K. Canis, J. Stevens, Z.-Y. Yang, A. Dell, S. M. Haslam, I. A. Wilson, G. J. Nabel (2008) Comparative Efficacy of Neutralizing Antibodies Elicited by Recombinant Hemagglutinin Proteins from Avian H5N1 Influenza Virus. Journal of Virology 82, 6200-6208.

U. Fiedler, U. Conrad (1995) High-level production and long-term storage of engineered antibodies in transgenic tobacco seeds. Biotechnology 13, 1090-1093.

M. E. Fraser, M. M. Chernaia, Y. V. Kozlov, M. N. G. James (1994) Crystal structure of the holotoxino from Shigella dysenteriae at 2.5 Å resolution. Nat. Struct. Biol. 1, 59-64.

M. E. Fraser, M. Fujinaga, M. M. Cherney, A. R. Melton-Celsa, E. M. Twiddy, A. D. O'Brien, M. N. James (2004) Structure of shiga toxin type 2 (Stx2) from *Escherichia coli* O157:H7. J. Biol. Chem. 279, 27511-7.

D. L. Harris, R. D. Glock (1972) Swine dysentery. J. Am. Vet. Med. Assoc. 160, 561-565.

J. Zimmermann, I. Saalbach, D. Jahn, M. Giersberg, S. Haehnel, J. Wedel, J. Macek, K. Zoufal, G. Glünder, D. Falkenburg, S. M. Kiprijanov (2009) Antibody expressing pea seeds as fodder for prevention of gastrointestinal parasitic infections in chickens. BMC Biotechnol. 9, 79.

V. Virdi, A. Coddens, S. De Buck, S. Millet, B. M. Goddeeris, E. Cox, H. De Greve, A. Depicker (2013) Orally fed seeds producing designer IgAs protect weaned piglets against enterotoxigenic *Escherichia coli* infection. PNAS 110, 11809-11814.

G. Habicht, C. Haupt, R. P. Friedrich, P. Hortschansky, C. Sachse, J. Meinhardt, K. Wieligmann, G. P. Gellermann, M. Brodhun, J. Götz, K.-J. Halbhuber, C. Röcken, U. Horn, M. Fändrich (2007) Directed selection of a conformational antibody domain that prevents mature amyloid fibril formation by stabilizing Aβ protofibrils. PNAS 104, 19232-19237.

A. J. Conley, J. J. Joensuu, A. M. Jevnikar, R. Menassa, J. E. Brandle (2009) Optimization of elastin-like polypeptide fusions for expression and purification of recombinant proteins in plants. Biotechnol. Bioeng. 103, 562-573.

M. R. Sudarshana, M. A. Plesha, S. L. Uratsu, B. W. Falk, A. M. Dandekar, T.-K. Huang, K. A. McDonald (2006) A chemically inducible cucumber mosaic virus amplicon system for expression of heterologous proteins in plant tissues. Plant Biotechnol. J. 4, 551-559.

H. T. Phan, U. Conrad (2016) Plant-based vaccine antigen production. Methods and Protocols. In: Vaccine Technologies for Veterinary Viral Diseases. Springer New York, N.Y., N.Y., 35-47.

U. Conrad, I. Plagmann, S. Malchow, M. Sack, D. M. Floss, A. A. Kruglov, S. A. Nedospasov, S. Rose-John, J. Scheller (2011) ELPylated anti-human TNF therapeutic single-domain antibodies for prevention of lethal septic shock. Plant Biotechnol. J. 9, 22-31.

M. Gahrtz, U. Conrad (2009) Immunomodulation of plant function by in vitro selected single-chain Fv intrabodies. In: L. Faye, V. Gomord (Eds.): Recombinant proteins from plants: methods and protocols. (Series: Methods in molecular biology, Vol. 483) Totowa, N.J.: Humana Press 289-312. World Organization for Animal Health (OIE) (2004) Highly pathogenic avian influenza, in manual of diagnostic tests and vaccines for terrestrial animals (Mammals, Birds, and Bees). Paris: World Organization for Animal Health (OIE), 259-269.

The invention claimed is:

1. A method for production of an oligomeric protein in eukaryotic cells comprising the steps
   a) Co-expression of two fusion proteins in eukaryotic cells comprising
      a first fusion protein comprising a protein and an S-Tag (in the following also called protein-S-Tag fusion protein),
      wherein the protein is an antigen or an antigen binding unit, and
      a second fusion protein comprising a S-protein and a tail piece (tp) (in the following also called S-protein-tail piece (tp) fusion protein),
      wherein the tail piece (tp) is an oligopeptide derived from a heavy chain of an IgM or IgA antibody,
   b) Extraction of the two fusion proteins,
   wherein oligomerisation of the protein of the protein-S-Tag fusion protein takes place after co-expression in eukaryotic cells according to step a) and/or after extraction according to step b).

2. The method of claim 1, wherein the eukaryotic cells are plant cells selected from a tobacco, soybean or *pisum* plant.

3. The method of claim 2, wherein the plant cells are cells of leaves or seeds of a plant.

4. The method of claim 2 or 3, wherein the co-expression according to step a) comprises the step
   provision of genes encoding the two fusion proteins in plant cells by co-infiltration of plant cells with *agrobacterium* strains.

5. The method of claim 1, wherein the antigen is an influenza hemagglutinin.

6. The Method of claim 1, wherein the antigen binding unit is an antibody against a pathogen of the gastrointestinal tract or the respiratory system.

7. The method of claim 1, wherein the S-Tag of the first fusion protein is at the C-terminus of the antigen or antigen binding unit.

8. The method of claim 1, wherein the oligomeric protein obtained is used for the manufacture of a vaccine.

9. The method of claim 1, wherein the tp is an oligopeptide with 15 to 25 amino acid residues.

10. The method of claim 9, wherein the tp comprises a sequence with at least 75% sequence identity to one of the sequences SEQ ID NOs: 16-22 or SEQ ID NOs: 30-34, wherein the position of the cysteine (Cys, C) residue is constant.

11. The method of claim 10, wherein the tp comprises one of the sequences SEQ ID NOs: 16-22 or SEQ ID NOs: 30-34 or a sequence with at least 85% sequence identity to one of the sequences SEQ ID NOs: 16-22 or SEQ ID NOs: 30-34, wherein the position of the cysteine (Cys, C) residue is constant.

12. An oligomeric protein comprising at least a first fusion protein comprising a protein and an S-Tag, in the following also called protein-S-Tag fusion protein,
   wherein the protein is an antigen or an antigen binding unit, and
   a second fusion protein comprising a S-protein and a tail piece (tp), in the following also called S-protein-tail piece (tp) fusion protein,
   wherein the tail piece (tp) is an oligopeptide derived from a heavy chain of an IgM or IgA antibody.

13. The oligomeric protein of claim 12, wherein the antigen is an influenza hemagglutinin.

14. The oligomeric protein of claim 12, wherein the antigen binding unit is an antibody against a pathogen of the gastrointestinal tract or the respiratory system.

15. The oligomeric protein of claim 12, wherein the S-Tag of the first fusion protein is at the C-terminus of the antigen or antigen binding unit.

16. The oligomeric protein of claim 12, wherein the tp is an oligopeptide with 15 to 25 amino acid residues.

17. The oligomeric protein of claim 16, comprising a sequence with at least 75%, sequence identity to one of the sequences SEQ ID NOs: 16-22 or SEQ ID NOs: 30-34, wherein the position of the cysteine (Cys, C) residue is constant.

18. The oligomeric protein of claim 17, comprising one of the sequences SEQ ID NOs: 16-22 or SEQ ID NOs: 30-34 or a sequence with at least 85% sequence identity to one of the sequences SEQ ID NOs: 16-22 or SEQ ID NOs: 30-34, wherein the position of the cysteine (Cys, C) residue is constant.

19. A nucleic acid comprising a nucleic acid sequence encoding an oligomeric protein of any one of the claims 12 to 18 or a vector comprising such a nucleic acid.

20. A cell or a non-human host organism comprising a nucleic acid or a vector of claim 19.

21. A vaccine comprising the oligomeric protein of any one of claims 12 to 18.

22. A vaccine comprising the oligomeric protein of claim 19.

* * * * *